United States Patent [19]
Gallo

[11] Patent Number: 5,834,234
[45] Date of Patent: Nov. 10, 1998

[54] APOPTOSIS ASSOCIATED PROTEIN BBK

[75] Inventor: Gregory J. Gallo, Reading, Mass.

[73] Assignee: ImmunoGen, Inc., Cambridge, Mass.

[21] Appl. No.: 632,514

[22] Filed: May 29, 1996

[51] Int. Cl.⁶ .............................. C12P 21/02; C07K 7/08; C07K 14/47; C12N 1/00; C12N 5/02
[52] U.S. Cl. .................. 435/69.1; 435/70.1; 435/71.1; 435/375; 435/243; 530/324; 530/325; 530/326; 530/327; 530/350
[58] Field of Search ...................................... 530/350, 324, 530/325, 326, 327; 514/12; 435/69.1, 70.1, 71.1, 243, 375

[56] References Cited

PUBLICATIONS

Boyd et al., Bik, a novel death–inducing protein shares a distinct sequent motif with Bcl–2 family proteins and interacts with viral and cellular survival–promoting proteins. Oncogene. 02 Nov. 1995, vol. 11, No. 9, pp. 1921–1928.

Chittenden et al., A conserved domain in Bak, distinct from BH1 and BH2, mediates cell death and protein binding functions. The EMBO Journal. 15 Nov. 1995, vol. 14, No. 22, pp. 5589–5596.

Ngo et al., The Protein Folding Problem and Tertiary Structure Prediction, Mertz et al (eds.), Birkhauser, Boston, 1994, pp. 433 and 492–495.

Krontiris, Molecular and Cellular Biology of Cancer, Internal Medicine, 4th edition, Stein (ed.), pp. 699–715.

*Primary Examiner*—Terry A. McKelvey
*Attorney, Agent, or Firm*—Hale and Dorr LLP

[57] ABSTRACT

The present invention is directed to an isolated Bbk protein, nucleotide sequences coding for and regulating expression of the protein, antibodies directed against the protein, and recombinant vectors and host cells containing the genetic sequences coding for and regulating the expression of the protein sequence. The invention is also directed to genomic DNA, cDNA, and RNA encoding the Bbk protein sequence and to corresponding antisense RNA sequences. Antibodies can be used to detect Bbk in biological specimens, including, for example, human tissue samples. The present invention is further directed to methods of treating degenerative disorders characterized in inappropriate cell proliferation or inappropriate cell death. The present invention is further directed to methods for diagnosing degenerative disorders characterized in inappropriate cell proliferation or inappropriate cell death, as well as methods for monitoring the progress of such degenerative disorders.

5 Claims, 17 Drawing Sheets

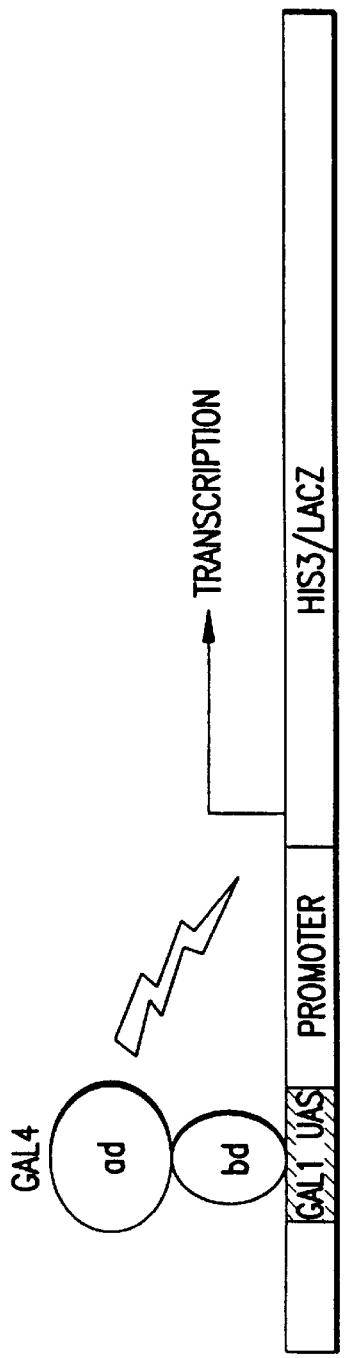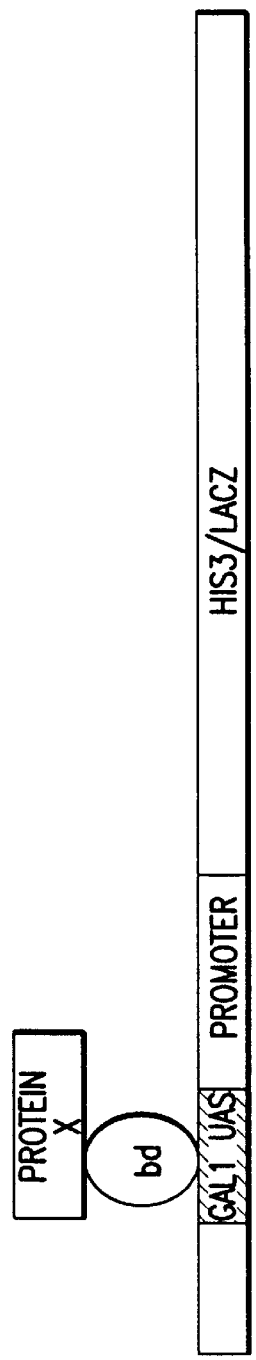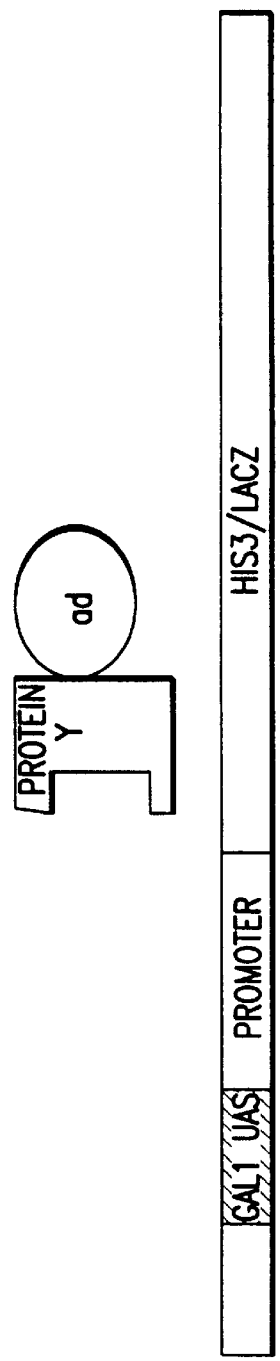
FIG.1A  FIG.1B

```
        10          20          30          40          50          60
    x    x      x    x      x    x    ,x    x      x    x      x    x
CGCAAGTTGA  GTGGAGGAGG  CGGCGGTGGG  GCCCCGGACC  AGGTGCCTCC  ATGGCAGGCT
GCGTTCAACT  CACCTCCTCC  GCCGCCACCC  CGGGGCCTGG  TCCACGGAGG  TACCGTCCGA
                                                            M  A  G⟩

70          80          90         100         110         120
    x    x      x    x      x    x      x    x      x    x      x    x
CTGAAGAGCT  GGGGCTCCGG  GAAGACACGC  TGAGGGTCCT  AGCTGCCTTC  CTTAGGCGTG
GACTTCTCGA  CCCCGAGGCC  CTTCTGTGCG  ACTCCCAGGA  TCGACGGAAG  GAATCCGCAC
 S  E  E  L   G  L  R   E  D  T   L  R  V  L   A  A  F   L  R  R⟩
                                        AAG
       130         140         150        |160         170         180
    x    x      x    x      x    x    ,x   x      x    x      x  , x
GTGAGGCTGC  CGGGTCTCCT  GTTCCAACTC  CACCTAGCCC  TGCCCAAGAA  GAGCCAACAG
CACTCCGACG  GCCCAGAGGA  CAAGGTTGAG  GTGGATCGGG  ACGGGTTCTT  CTCGGTTGTC
 G  E  A  A   G  S  P   V  P  T   P  P  S  P   A  Q  E   E  P  T⟩

190         200         210         220         230         240
    x    x      x    x      x    x      x    x      x    x      x    x
ACTTCCTGAG  CCGCCTTCGA  AGATGTCTTC  CCTGCTCCCT  GGGGCGAGGA  GCAGCCCCCT
TGAAGGACTC  GGCGGAAGCT  TCTACAGAAG  GGACGAGGGA  CCCCGCTCCT  CGTCGGGGGA
 D  F  L  S   R  L  R   R  C  L   P  C  S  L   G  R  G   A  A  P⟩

250         260         270         280         290         300
   ,x    x      x    x      x    x      x    x      x    x      x    x
CTGAGTCCCC  TCGGCCTTGC  TCTCTGCCCA  TCCGCCCCTG  CTATGGTTTA  GAGCCTGGCC
GACTCAGGGG  AGCCGGAACG  AGAGACGGGT  AGGCGGGGAC  GATACCAAAT  CTCGGACCGG
 S  E  S  P   R  P  C   S  L  P   I  R  P  C   Y  G  L   E  P  G⟩

310         320         330         340         350         360
    x    x      x    x      x    x      x    x      x    x      x    x
CAGCTACTCC  AGACTTCTAT  GCTTTGGTGG  CCCAGCGGCT  GGAACAGCTG  GTCCAAGAGC
GTCGATGAGG  TCTGAAGATA  CGAAACCACC  GGGTCGCCGA  CCTTGTCGAC  CAGGTTCTCG
 P  A  T  P   D  F  Y   A  L  V   A  Q  R  L   E  Q  L   V  Q  E⟩

370         380         390         400         410         420
   ,x    x      x    x      x    x      x    x      x    x      x    x
AGCTGAAATC  TCCGCCCAGC  CCAGAATTAC  AGGGTCCCCC  ATCGACAGAG  AAGGAAGCCA
TCGACTTTAG  AGGCGGGTCG  GGTCTTAATG  TCCCAGGGGG  TAGCTGTCTC  TTCCTTCGGT
 Q  L  K  S   P  P  S   P  E  L   Q  G  P  P   S  T  E   K  E  A⟩

430         440         450         460         470         480
    x    x      x    x      x    x      x    x      x    x      x    x
TACTGCGGAG  GCTGGTGGCC  CTGCTGGAGG  AGGAGGCAGA  AGTCATTAAC  CAGAAGCTGG
ATGACGCCTC  CGACCACCGG  GACGACCTCC  TCCTCCGTCT  TCAGTAATTG  GTCTTCGACC
 I  L  R  R   L  V  A   L  L  E   E  E  A  E   V  I  N   Q  K  L⟩
```

FIG.2A

```
         490        500        510        520        530        540
          x  x       x  x       x  x       x  x       x  x       x  x
     CCTCGGACCC CGCCCTGCGC AGCAAGCTGG TCCGCCTGTC CTCCGACTCT TTCGCCCGCC
     GGAGCCTGGG GCGGGACGCG TCGTTCGACC AGGCGGACAG GAGGCTGAGA AAGCGGGCGG
      A  S  D  P   A  L  R   S  K  L   V  R  L  S   S  D  S   F  A  R>

550        560        570        580        590        600
          x  x       x  x       x  x       x  x       x  x       x  x
     TGGTGGAGCT GTTCTGTAGC CGGGATGACA GCTCTCGCCC AAGCCGAGCA TGCCCCGGGC
     ACCACCTCGA CAAGACATCG GCCCTACTGT CGAGAGCGGG TTCGGCTCGT ACGGGGCCCG
      L  V  E  L   F  C  S   R  D  D   S  S  R  P   S  R  A   C  P  G>

610        620        630        640        650        660
          x  x       x  x       x  x       x  x       x  x       x  x
     CCCCGCCTCC TTCCCCGGAG CCCCTGGCCC GCCTGGCCCT AGCCATGGAG CTGAGCCGGC
     GGGGCGGAGG AAGGGGCCTC GGGGACCGGG CGGACCGGGA TCGGTACCTC GACTCGGCCG
      P  P  P  P   S  P  E   P  L  A   R  L  A  L   A  M  E   L  S  R>

670        680        690        700        710        720
          x  x       x  x       x  x       x  x       x  x       x  x
     GCGTGGCCGG GCTGGGGGGC ACCCTGGCCG GACTCAGCGT GGAGCACGTG CACAGCTTCA
     CGCACCGGCC CGACCCCCCG TGGGACCGGC CTGAGTCGCA CCTCGTGCAC GTGTCGAAGT
      R  V  A  G   L  G  G   T  L  A   G  L  S  V   E  H  V   H  S  F>

730        740        750        760        770        780
          x  x       x  x       x  x       x  x       x  x       x  x
     CGCCCTGGAT CCAGGCCCAC GGGGGCTGGG AGGGCATCCT GGCTGTTTCA CCCGTGGACT
     GCGGGACCTA GGTCCGGGTG CCCCCGACCC TCCCGTAGGA CCGACAAAGT GGGCACCTGA
      T  P  W  I   Q  A  H   G  G  W   E  G  I  L   A  V  S   P  V  D>

790        800        810        820        830        840
          x  x       x  x       x  x       x  x       x  x       x  x
     TGAACTTGCC ATTGGACTGA GCTCTTTCTC AGAAGCTGCT ACAAGATGAC ACCTCATGTC
     ACTTGAACGG TAACCTGACT CGAGAAAGAG TCTTCGACGA TGTTCTACTG TGGAGTACAG
      L  N  L  P   L  D  *> [SEQ ID NO:11]

850        860        870        880        890        900
          x  x       x  x       x  x       x  x       x  x       x  x
     CCTGCCCTCT TCGTGTGCTT TTCCAAGTCT TCCTATTCCA CTCAGGGCTG TGGGGTGGTG
     GGACGGGAGA AGCACACGAA AAGGTTCAGA AGGATAAGGT GAGTCCCGAC ACCCCACCAC 910        920        930        940        950
          x  x       x  x       x  x       x  x       x  x
     GTTGCCCTAC CTGTTTTTGC CAAAAATAAA TTGTTTAAAA CTTTTCTTAT TAAAAACG [SEQ ID NO:9]
     CAACGGGATG GACAAAAACG GTTTTTATTT AACAAATTTT GAAAAGAATA ATTTTTGC [SEQ ID NO:10]
```

FIG.2B

BH2 DOMAIN

| | | | | | | | | | | | | | | | |
|---|---|---|---|---|---|---|---|---|---|---|---|---|---|---|---|
| BBK | 226 | W I Q | . | A | H | G G W E | G | I | L | A | V | [SEQ ID NO:12] |
| BAK | 170 | W I A | . | Q | R | G G W V | A | A | L | N | L | [SEQ ID NO:13] |
| BAX | 151 | W I Q | . | D | Q | G G W D | G | L | L | S | Y | [SEQ ID NO:14] |
| BIK | 122 | W R S | P | N | P | G S W V | S | C | E | Q | V | [SEQ ID NO:15] |
| BCL-2 | 188 | W I Q | . | D | N | G G W D | A | F | V | E | L | [SEQ ID NO:16] |
| BCL-X | 181 | W I Q | . | E | N | G G W D | T | F | V | E | L | [SEQ ID NO:17] |

FIG.8A

BH3 DOMAIN

| | | | | | | | | | | | | |
|---|---|---|---|---|---|---|---|---|---|---|---|---|
| BBK | 125 | L R R L V A L L E E E A E | [SEQ ID NO:18] |
| BAK | 74 | V G R Q L A I I G D D I N | [SEQ ID NO:19] |
| BAX | 59 | L S E C L K R I G D E L D | [SEQ ID NO:20] |
| BIK | 57 | L A L R L A C I G D E M D | [SEQ ID NO:21] |
| BCL-2 | 93 | V H L A L R Q A G D D F S | [SEQ ID NO:22] |
| BCLX | 86 | V K Q A L R E A G D E F E | [SEQ ID NO:23] |

FIG.8B

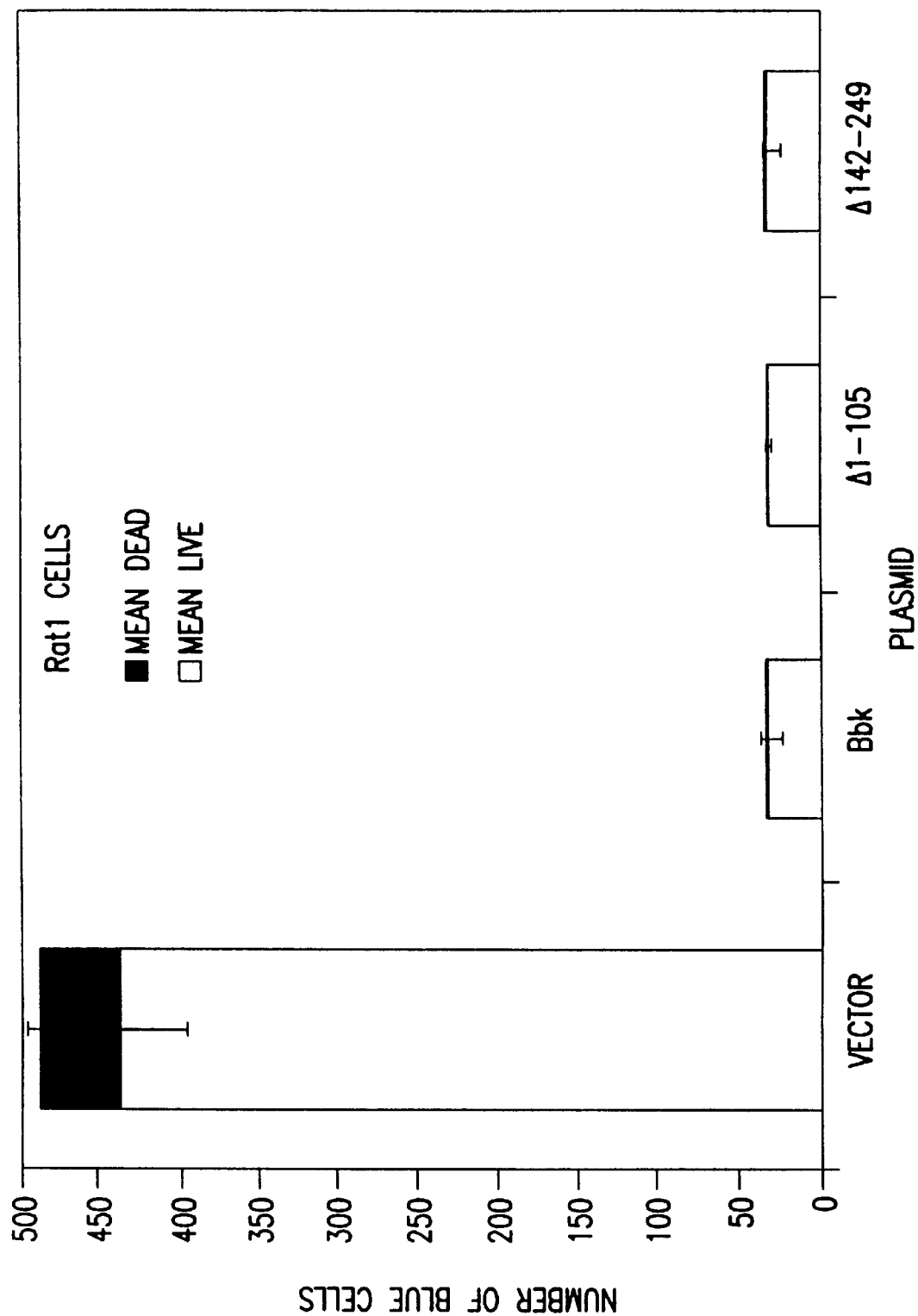

```
BBK        125   L R R L V A L L E E E A E    [SEQ ID NO:24]
PM-LVLEE   125   A R R L A A L A E A A A E    [SEQ ID NO:25]
PM-V       125   L R R L A A L L E E E A E    [SEQ ID NO:26]
PM-L       125   L R R L V A L A E E E A E    [SEQ ID NO:27]
PM-EE      125   L R R L V A L L E A A A E    [SEQ ID NO:28]
```

FIG.9B

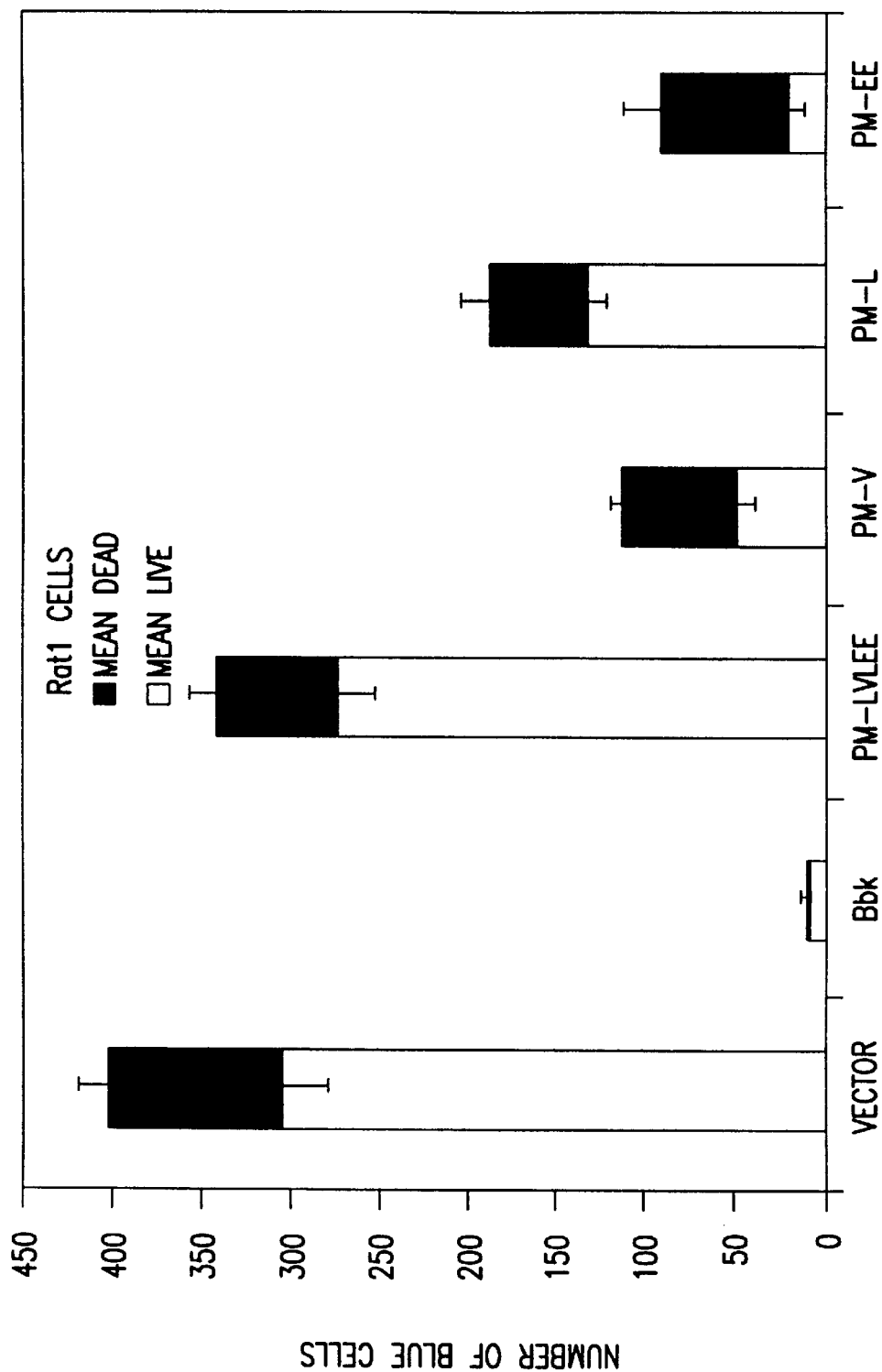

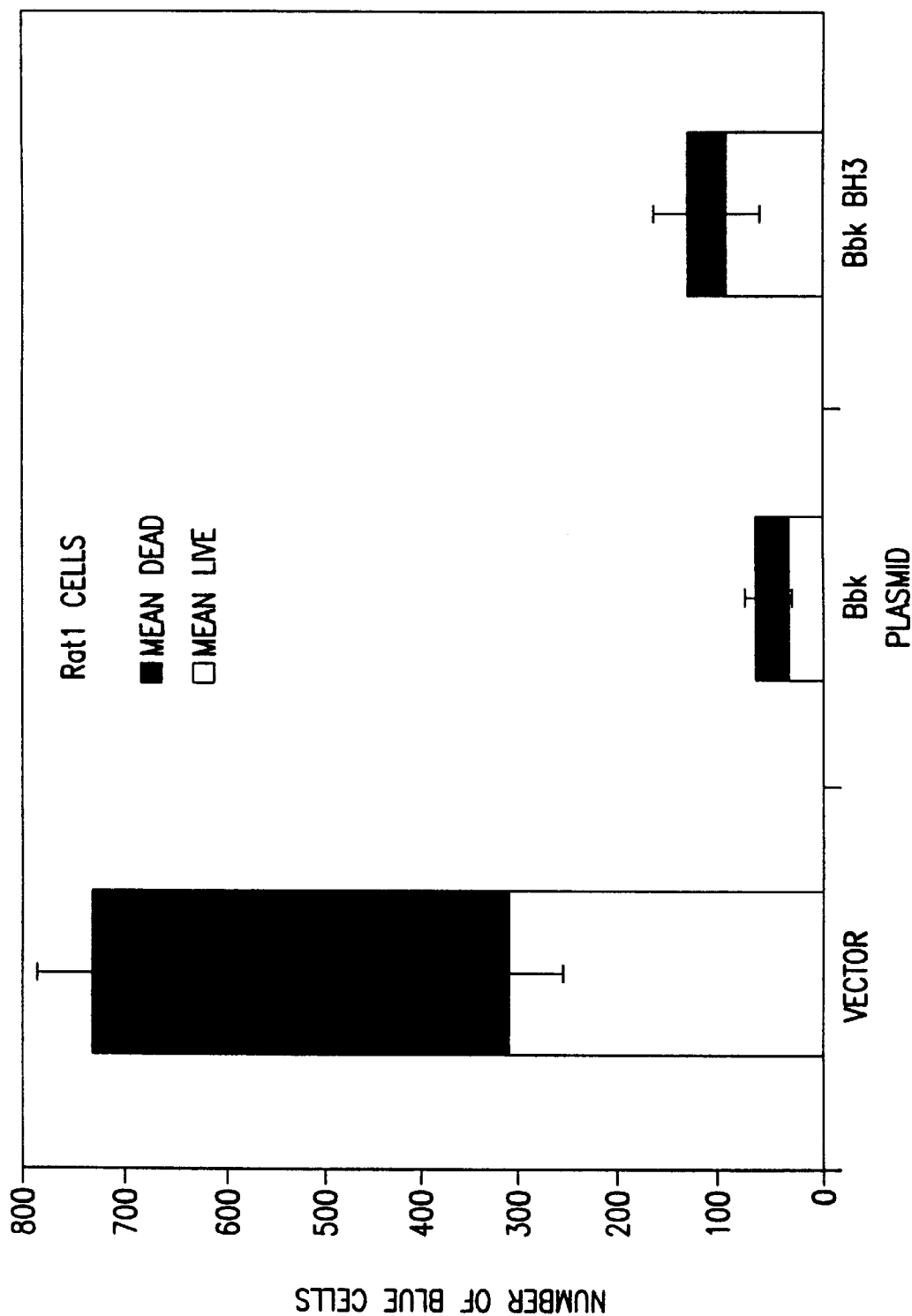

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 13 amino acid
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Leu Arg Arg Leu Val Ala Leu Leu Glu Glu Glu Ala Glu
                          5                      10

( 2 ) INFORMATION FOR SEQ ID NO:2:

( i ) SEQUENCE CHARACTERISTICS:
        ( A ) LENGTH: 13 amino acid
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Leu Arg Arg Leu Ala Ala Leu Leu Glu Glu Glu Ala Glu
                          5                      10

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Leu Arg Arg Leu Val Ala Leu Ala Glu Glu Glu Ala Glu
                          5                      10

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Leu Arg Arg Leu Val Ala Leu Leu Glu Ala Ala Ala Glu
                          5                      10

( 2 ) INFORMATION FOR SEQ ID NO:5:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

Leu Arg Arg Leu Val Ala Leu Leu Glu Glu Glu Ala Glu
      5         10

( 2 ) INFORMATION FOR SEQ ID NO:6:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

Leu Arg Arg Leu Ala Ala Leu Leu Glu Glu Glu Ala Glu
      5         10

( 2 ) INFORMATION FOR SEQ ID NO:7:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

Leu Arg Arg Leu Val Ala Leu Ala Glu Glu Glu Ala Glu
      5         10

( 2 ) INFORMATION FOR SEQ ID NO:8:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

Leu Arg Arg Leu Val Ala Leu Leu Glu Ala Ala Ala Glu
      5         10

( 2 ) INFORMATION FOR SEQ ID NO:9:

( i ) SEQUENCE CHARACTERISTICS:
    ( A ) LENGTH: 958 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

CGCAAGTTGA GTGGAGGAGG CGGCGGTGGG GCCCCGGACC AGGTGCCTCC ATGGCAGGCT  60

| | | | | | |
|---|---|---|---|---|---|
| CTGAAGAGCT | GGGGCTCCGG | GAAGACACGC | TGAGGGTCCT | AGCTGCCTTC | CTTAGGCGTG | 120 |
| GTGAGGCTGC | CGGGTCTCCT | GTTCCAACTC | CACCTAGCCC | TGCCCAAGAA | GAGCCAACAG | 180 |
| ACTTCCTGAG | CCGCCTTCGA | AGATGTCTTC | CCTGCTCCCT | GGGGCGAGGA | GCAGCCCCT | 240 |
| CTGAGTCCCC | TCGGCCTTGC | TCTCTGCCCA | TCCGCCCCTG | CTATGGTTTA | GAGCCTGGCC | 300 |
| CAGCTACTCC | AGACTTCTAT | GCTTTGGTGG | CCCAGCGGCT | GGAACAGCTG | GTCCAAGAGC | 360 |
| AGCTGAAATC | TCCGCCCAGC | CCAGAATTAC | AGGGTCCCCC | ATCGACAGAG | AAGGAAGCCA | 420 |
| TACTGCGGAG | GCTGGTGGCC | CTGCTGGAGG | AGGAGGCAGA | AGTCATTAACCAGAAGCTGG | | 480 |
| CCTCGGACCC | CGCCCTGCGC | AGCAAGCTGG | TCCGCCTGTC | CTCCGACTCT | TTCGCCCGCC | 540 |
| TGGTGGAGCT | GTTCTGTAGC | CGGGATGACA | GCTCTCGCCC | AAGCCGAGCA | TGCCCCGGGC | 600 |
| CCCCGCCTCC | TTCCCCGGAG | CCCCTGGCCC | GCCTGGCCCT | AGCCATGGAG | CTGAGCCGGC | 660 |
| GCGTGGCCGG | GCTGGGGGGC | ACCCTGGCCG | GACTCAGCGT | GGAGCACGTG | CACAGCTTCA | 720 |
| CGCCCTGGAT | CCAGGCCCAC | GGGGGCTGGG | AGGGCATCCT | GGCTGTTTCA | CCCGTGGACT | 780 |
| TGAACTTGCC | ATTGGACTGA | GCTCTTTCTC | AGAAGCTGCT | ACAAGATGAC | ACCTCATGTC | 840 |
| CCTGCCCTCT | TCGTGTGCTT | TTCCAAGTCT | TCCTATTCCA | CTCAGGGCTG | TGGGGTGGTG | 900 |
| GTTGCCCTAC | CTGTTTTTGC | CAAAAATAAA | TTGTTTAAAA | CTTTTCTTAT | TAAAAACG | 958 |

( 2 ) INFORMATION FOR SEQ ID NO:10:

( i ) SEQUENCE CHARACTERISTICS:
    ( A ) LENGTH: 958 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

| | | | | | |
|---|---|---|---|---|---|
| GCGTTCAACT | CACCTCCTCC | GCCGCCACCC | CGGGGCCTGG | TCCACGGAGG | TACCGTCCGA | 60 |
| GACTTCTCGA | CCCCGAGGCC | CTTCTGTGCG | ACTCCCAGGA | TCGACGGAAG | GAATCCGCAC | 120 |
| CACTCCGACG | GCCCAGAGGA | CAAGGTTGAG | GTGGATCGGG | ACGGGTTCTT | CTCGGTTGTC | 180 |
| TGAAGGACTC | GGCGGAAGCT | TCTACAGAAG | GGACGAGGGA | CCCCGCTCCT | CGTCGGGGA | 240 |
| GACTCAGGGG | AGCCGGAACG | AGAGACGGGT | AGGCGGGGAC | GATACCAAAT | CTCGGACCGG | 300 |
| GTCGATGAGG | TCTGAAGATA | CGAAACCACC | GGGTCGCCGA | CCTTGTCGAC | CAGGTTCTCG | 360 |
| TCGACTTTAG | AGGCGGGTCG | GGTCTTAATG | TCCCAGGGGG | TAGCTGTCTC | TTCCTTCGGT | 420 |
| ATGACGCCTC | CGACCACCGG | GACGACCTCC | TCCTCCGTCT | TCAGTAATTG | GTCTTCGACC | 480 |
| GGAGCCTGGG | GCGGGACGCG | TCGTTCGACC | AGGCGGACAG | GAGGCTGAGA | AAGCGGGCGG | 540 |
| ACCACCTCGA | CAAGACATCG | GCCCTACTGT | CGAGAGCGGG | TTCGGCTCGT | ACGGGCCCG | 600 |
| GGGGCGGAGG | AAGGGGCCTC | GGGGACCGGG | CGGACCGGGA | TCGGTACCTC | GACTCGGCCG | 660 |
| CGCACCGGCC | CGACCCCCCG | TGGGACCGGC | CTGAGTCGCA | CCTCGTGCAC | GTGTCGAAGT | 720 |
| GCGGGACCTA | GGTCCGGGTG | CCCCCGACCC | TCCCGTAGGA | CCGACAAAGT | GGGCACCTGA | 780 |
| ACTTGAACGG | TAACCTGACT | CGAGAAAGAG | TCTTCGACGA | TGTTCTACTG | TGGAGTACAG | 840 |
| GGACGGGAGA | AGCACACGAA | AAGGTTCAGA | AGGATAAGGT | GAGTCCCGAC | ACCCCACCAC | 900 |
| CAACGGGATG | GACAAAAACG | GTTTTTATTT | AACAAATTTT | GAAAGAATA | ATTTTTGC | 958 |

( 2 ) INFORMATION FOR SEQ ID NO:11:

( i ) SEQUENCE CHARACTERISTICS:
    ( A ) LENGTH: 249 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

| Met | Ala | Gly | Ser | Glu | Glu | Leu | Gly | Leu | Arg | Glu | Asp | Thr | Leu | Arg |
|---|---|---|---|---|---|---|---|---|---|---|---|---|---|---|
| 1 | | | | 5 | | | | | 10 | | | | | 15 |
| Val | Leu | Ala | Ala | Phe | Leu | Arg | Arg | Gly | Glu | Ala | Ala | Gly | Ser | Pro |
| | | | | 20 | | | | | 25 | | | | | 30 |
| Val | Pro | Thr | Pro | Pro | Ser | Pro | Ala | Gln | Glu | Pro | Thr | Asp | Phe |
| | | | | 35 | | | | | 40 | | | | | 45 |
| Leu | Ser | Arg | Leu | Arg | Arg | Cys | Leu | Pro | Cys | Ser | Leu | Gly | Arg | Gly |
| | | | | 50 | | | | | 55 | | | | | 60 |
| Ala | Ala | Pro | Ser | Glu | Ser | Pro | Arg | Pro | Cys | Ser | Leu | Pro | Ile | Arg |
| | | | | 65 | | | | | 70 | | | | | 75 |
| Pro | Cys | Tyr | Gly | Leu | Glu | Pro | Gly | Pro | Ala | Thr | Pro | Asp | Phe | Tyr |
| | | | | 80 | | | | | 85 | | | | | 90 |
| Ala | Leu | Val | Ala | Gln | Arg | Leu | Glu | Gln | Leu | Val | Gln | Glu | Gln | Leu |
| | | | | 95 | | | | | 100 | | | | | 105 |
| Lys | Ser | Pro | Pro | Ser | Pro | Glu | Leu | Gln | Gly | Pro | Pro | Ser | Thr | Glu |
| | | | | 110 | | | | | 115 | | | | | 120 |
| Lys | Glu | Ala | Ile | Leu | Arg | Arg | Leu | Val | Ala | Leu | Leu | Glu | Glu | Glu |
| | | | | 125 | | | | | 130 | | | | | 135 |
| Ala | Glu | Val | Ile | Asn | Gln | Lys | Leu | Ala | Ser | Asp | Pro | Ala | Leu | Arg |
| | | | | 140 | | | | | 145 | | | | | 150 |
| Ser | Lys | Leu | Val | Arg | Leu | Ser | Ser | Asp | Ser | Phe | Ala | Arg | Leu | Val |
| | | | | 155 | | | | | 160 | | | | | 165 |
| Glu | Leu | Phe | Cys | Ser | Arg | Asp | Asp | Ser | Ser | Arg | Pro | Ser | Arg | Ala |
| | | | | 170 | | | | | 175 | | | | | 180 |
| Cys | Pro | Gly | Pro | Pro | Pro | Pro | Ser | Pro | Glu | Pro | Leu | Ala | Arg | Leu |
| | | | | 185 | | | | | 190 | | | | | 195 |
| Ala | Leu | Ala | Met | Glu | Leu | Ser | Arg | Arg | Val | Ala | Gly | Leu | Gly | Gly |
| | | | | 200 | | | | | 205 | | | | | 210 |
| Thr | Leu | Ala | Gly | Leu | Ser | Val | Glu | His | Val | His | Ser | Phe | Thr | Pro |
| | | | | 215 | | | | | 220 | | | | | 225 |
| Trp | Ile | Gln | Ala | His | Gly | Gly | Trp | Glu | Gly | Ile | Leu | Ala | Val | Ser |
| | | | | 230 | | | | | 235 | | | | | 240 |
| Pro | Val | Asp | Leu | Asn | Leu | Pro | Leu | Asp |
| | | | | 245 |

(2) INFORMATION FOR SEQ ID NO:12:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

| Trp | Ile | Gln | Ala | His | Gly | Gly | Trp | Glu | Gly | Ile | Leu | Ala | Val |
|---|---|---|---|---|---|---|---|---|---|---|---|---|---|
| 1 | | | | 5 | | | | | 10 | | | | |

(2) INFORMATION FOR SEQ ID NO:13:

(i) SEQUENCE CHARACTERISTICS:
(A) LENGTH: 14 amino acids (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:13:

Trp Ile Ala Gln Arg Gly Gly Trp Val Ala Ala Leu Asn Leu
                  5                   10

(2) INFORMATION FOR SEQ ID NO:14:

(i) SEQUENCE CHARACTERISTICS:
      (A) LENGTH: 14 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:14:

Trp Ile Gln Asp Gln Gly Gly Trp Asp Gly Leu Leu Ser Tyr
                  5                   10

(2) INFORMATION FOR SEQ ID NO:15:

(i) SEQUENCE CHARACTERISTICS:
      (A) LENGTH: 15 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:15:

Trp Arg Ser Pro Asn Pro Gly Ser Trp Val Ser Cys Glu Gln Val
                  5                   10                  15

(2) INFORMATION FOR SEQ ID NO:16:

(i) SEQUENCE CHARACTERISTICS:
      (A) LENGTH: 14 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:16:

Trp Ile Gln Asp Asn Gly Gly Trp Asp Ala Phe Val Glu Leu
                  5                   10

(2) INFORMATION FOR SEQ ID NO:17:

(i) SEQUENCE CHARACTERISTICS:
      (A) LENGTH: 14 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:17:

Trp Ile Gln Glu Asn Gly Gly Trp Asp Thr Phe Val Glu Leu
                  5                   10

(2) INFORMATION FOR SEQ ID NO:18:

(i) SEQUENCE CHARACTERISTICS:
      (A) LENGTH: 13 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:18:

Leu Arg Arg Leu Val Ala Leu Leu Glu Glu Glu Ala Glu
                      5                        10

(2) INFORMATION FOR SEQ ID NO:19:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:19:

Val Gly Arg Gln Leu Ala Ile Ile Gly Asp Asp Ile Asn
                      5                        10

(2) INFORMATION FOR SEQ ID NO:20:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:20:

Leu Ser Glu Cys Leu Lys Arg Ile Gly Asp Glu Leu Asp
                      5                        10

(2) INFORMATION FOR SEQ ID NO:21:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:21:

Leu Ala Leu Arg Leu Ala Cys Ile Gly Asp Glu Met Asp
                      5                        10

(2) INFORMATION FOR SEQ ID NO:22:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:22:

Val His Leu Ala Leu Arg Gln Ala Gly Asp Asp Phe Ser
                      5                        10

(2) INFORMATION FOR SEQ ID NO:23:

(i) SEQUENCE CHARACTERISTICS:
(A) LENGTH: 13 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:23:

Val Lys Gln Ala Leu Arg Glu Ala Gly Asp Glu Phe Glu
                 5                       10

(2) INFORMATION FOR SEQ ID NO:24:

(i) SEQUENCE CHARACTERISTICS:
    (A) LENGTH: 13 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:24:

Leu Arg Arg Leu Val Ala Leu Leu Glu Glu Glu Ala Glu
                 5                       10

(2) INFORMATION FOR SEQ ID NO:25:

(i) SEQUENCE CHARACTERISTICS:
    (A) LENGTH: 13 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:25:

Ala Arg Arg Leu Ala Ala Leu Ala Glu Ala Ala Ala Glu
                 5                       10

(2) INFORMATION FOR SEQ ID NO:26:

(i) SEQUENCE CHARACTERISTICS:
    (A) LENGTH: 13 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:26:

Leu Arg Arg Leu Ala Ala Leu Leu Glu Glu Glu Ala Glu
                 5                       10

(2) INFORMATION FOR SEQ ID NO:27:

(i) SEQUENCE CHARACTERISTICS:
    (A) LENGTH: 13 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:27:

Leu Arg Arg Leu Val Ala Leu Ala Glu Glu Glu Ala Glu
                 5                       10

(2) INFORMATION FOR SEQ ID NO:28:

(i) SEQUENCE CHARACTERISTICS:
    (A) LENGTH: 13 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:28:

Leu Arg Arg Leu Val Ala Leu Leu Glu Ala Ala Ala Glu
                  5                     10

(2) INFORMATION FOR SEQ ID NO:29:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:29:

Met Gly Tyr Pro Tyr Asp Val Pro Asp Tyr Ala Ser Leu Ser
                  5                     10

APOPTOSIS ASSOCIATED PROTEIN BBK

FIELD OF THE INVENTION

The present invention relates generally to the field of cell physiology, and more particularly, to apoptosis. Even more particularly, the present invention is related to the novel apoptosis associated protein Bbk; to nucleotide sequences encoding Bbk; to products and processes involved in the cloning, preparation and expression of genes and nucleotide sequences encoding Bbk; to antibodies with specificity to Bbk; and to diagnostic and therapeutic uses of the above.

BACKGROUND OF THE INVENTION

"Apoptosis" refers to cell suicide that proceeds by an active, physiological process (Kerr, J. F., et al., *Br. J. Cancer* 26:239–257 (1972); Wyllie, A. H., *Nature* 284:555–556 (1980)). Cells that die by apoptosis undergo characteristic morphological changes, including cell shrinkage, and nuclear condensation and fragmentation. Apoptosis plays an important role in developmental processes, including morphogenesis, maturation of the immune system, and tissue homeostasis whereby cell numbers are limited in tissues that are continually renewed by cell division (Ellis, R. E., et al., *Annu. Rev. Cell. Biol.*7:663–698 (1991); Oppenheim, R. W., et al., *Neurosci.* 14:453–501 (1991); Cohen, J. J., et al., *Annul. Rev. Imnnitnol.* 10:267–293 (1992); Raff, M. C., *Nature* 356:397–400 (1992)). Apoptosis is an important cellular safeguard against tumorigenesis (Williams, G. T., *Cell* 65:1097–1098 (1991); Lane, D. P. *Nature* 362:786–787 (1993)). Defects in the apoptotic pathway may contribute to the onset or progression of malignancies. Under certain conditions, cells undergo apoptosis in response to forced expression of oncogenes, or other genes that drive cell proliferation; (Askew, D., et al., *Oncogene* 6:195–1922 (1991); Evan, G. I., et al., *Cell* 69:119–128 (1992); Rao, L., et al., *Proc. Natl. Acad Sci. USA* 89:7742–7746 (1992); Smeyne, R. J., et al., *Nature* 363:166–169 (1993)). A variety of degenerative disorders may involve aberrant apoptosis, resulting in premature or inappropriate cell death (Barr, P. J., et al., *Biotechnology* 12:487–493 (1994)). Productive infection by certain viruses may depend on suppression of host cell death by anti-apoptotic viral gene products (Rao, L., et al., *Proc. Natl. Acad. Sci. USA* 89:7742–7746 (1992); Ray, C. A., et al., *Cell* 69:597–604 (1992); White, E., et al., *Mol. Cell. Biol.* 12:2570–2580 (1992); Vaux, D. L., et al., *Cell* 76:777–779 (1994), and inhibition of apoptosis can alter the course (i.e. lytic vs. latent) of viral infection; (Levine, B., et al., *Nature* 361:739–742 (1993)). Widespread apoptosis of T lymphocytes triggered by HIV infection may, at least in part, be responsible for the immune system failure associated with AIDS (Gougeon M., et al., *Science* 260:1269–1270 (1993)). The roles of apoptosis in normal and pathological cell cycle events are reviewed in Holbrook, N.J., et al., Eds., *Cellular Aging and Cell Death*, Wiley-Liss, Inc., Publisher, New York, N.Y. (1996).

The bcl-2 gene product has been intensively studied as a potent suppressor of apoptotic cell death. The bcl-2 gene was originally identified at the t(14:18) translocation breakpoint that occurs frequently in human B cell follicular lymphomas (Bakhshi, A., et al., *Cell* 41:899–906 (1985); Cleary, M. L., et al., *Proc. Natl. Acad. Sci. USA* 82: (1985); Tsujimoto, Y., et al., *Science* 229:1390–1393 (1985)). This translocation results in the constitutive activation of bcl-2 gene expression due to juxtaposition with the immunoglobulin heavy chain locus. Bcl-2 functions as an oncogene in this disease by inappropriately suppressing apoptosis that would normally limit the accumulation of these cells (McDonnell, T. J., et al., *Cell* 57:79–88 (1989); Hockenbery, D., et cal., *Nature* 348:334–336 (1990)). Consequently, B cells accumulate during the indolent stage of the lymphoma due to their failure to die rather than by uncontrolled proliferation.

The anti-apoptotic activity of Bcl-2 is not restricted to B cells. A large number of studies have demonstrated that ectopic Bcl-2 expression can suppress apoptosis triggered by diverse stimuli in a multitude of cell lineages (Vaux, D. L., et al., *Nature* 335:440–442 (1988); Sentman, C. L., et al., *Cell* 67:879–888 (1991); Strasser, A., et al., *Cell* 67:889–899 (1991); Hockenbery, D. M., et al., *Cell* 75:241–251 (1993)). Bcl-2 blocks cell death induced by growth factor withdrawal, DNA damage, oncogene expression, oxidative stress, and viral infection. The ability of Bcl-2 to block apoptosis in virtually every system suggests that Bcl-2 is closely connected with the machinery that actually carries out the death program. This view is further supported by the conservation of Bcl-2 function across species. The ced9 gene in the nematode *C. elegans* functions to suppress programmed death in certain cell lineages of the developing worm (Ellis, H. M., et al, *Cell* 44:817–829 (1986)). Ced9 appears to be a functional homologue of Bcl-2, since Bcl-2 can complement ced9 in transgenic worms (Vaux, D. L., et al., *Science* 258:1955–1957 (1991)). Bcl-2 can also function in insect cells as demonstrated by the ability of Bcl-2 to suppress apoptosis induced by Baculovirus infection (Alnemri, E. S., et al., *Proc. Natl. Acad. Sci. USA* 89:7295–7299 (1992)). The molecular mechanism whereby Bcl-2 operates to block cell death is poorly understood.

Additional cellular genes that exhibit significant sequence homology with Bcl-2 have been identified and, where tested, these genes appear also to function as regulators of apoptotic cell death. One Bcl-2 relative, Bcl-X, was isolated by low stringency DNA hybridization to the Bcl-2 gene (Boise, L. H., et al., *Cell* 74:597–608 (1993)). The Bcl-X RNA is differentially spliced to produce a long form, termed Bcl-$X_L$, and a shorter forn, Bcl-$X_S$, bearing a short internal deletion. Bcl-$X_L$, functions to suppress cell death, much like Bcl-2, whereas the deleted form, Bcl-$X_S$, can inhibit protection by Bcl-2 and may function as a "dominant negative" species. A second Bcl-2 relative, Bax, was identified biochemically as protein found in co-immunoprecipitates with Bcl-2 (Oltvai, Z. N., et al., *Cell* 74:609–619 (1993)). Isolation of the corresponding cDNA revealed that the Bax protein shows substantial sequence homology to Bcl-2. Bax forms heterodimers with Bcl-2 and appears to induce apoptosis and function as a negative regulator of Bcl-2 function. Ectopic expression of Bax was shown to block the protection against apoptosis afforded by Bcl-2 expression.

Two additional cellular Bcl-2 relatives, Mcl-1 and Al(Kozopas, K. M., et al., *Proc. Natl. Acad. Sci. USA* 90:3516–3520 (1993); Lin, E. Y., et al., *J. Immunol.* 1.51:1979–1988 (1993)) were originally isolated as mRNAs induced in response to specific stimuli: phorbol ester induced differentiation of mycloid leukemia cells (Mcl-1); and GM-CSF treatment of murine bone marrow cells (A1). It is not yet known whether either Mcl-1 or A1 can modulate apoptosis.

In addition to these cellular Bcl-2 relatives, a number of Bcl-2 homologues encoded by DNA viruses have been identified. The Epstein-Barr virus BHRF-1 gene product was noted to contain sequence homology to Bcl-2 and has subsequently been shown to function as a suppressor of apoptosis (Henderson, et al., *Proc. Natl. Acad. Sci. USA*

90:8479–8488 (1993)). Likewise, the African swine fever virus LMW5-HL gene encodes a protein structurally similar to Bcl-2 (Neilan, J. G., et al., *J. Virol.* 67:4391–4394 (1993)). The Adenovirus E1b 19kD protein appears to be functionally equivalent to Bcl-2, although the primary sequence homology is quite limited (White, E., et al., *Mol. Cell. Biol.* 12:2570–2580 (1992)). It is likely that these genes function to ensure replication of viral DNA by preventing apoptosis of the infected cell. The finding that unrelated DNA viruses have evolved genes that apparently function to mimic the action of Bcl-2, supports the conclusion that Bcl-2 represents an important apoptosis regulator.

The isolation and characterization of a bcl-2 related gene, termed bak, is described in co-pending U.S. application Ser. No. 08/321,071, filed 11 Oct., 1994, U.S. Pat. No. 5,672,686 which is a continuation-in-part of U.S. application Ser. No. 8/287,427, filed 9 Aug., 1994, abandoned (bak is referred to therein as bcl-y), the disclosures of which are incorporated herein by reference. Ectopic Bak expression accelerates the death of an IL-3 dependent cell line upon cytokine withdrawal, and opposes the protection against apoptosis afforded by Bcl-2. In addition, enforced expression of Bak is sufficient to induce apoptosis of serum deprived fibroblasts, raising the possibility that Bak directly activates, or is itself a component of, the cell death machinery.

Known cellular Bcl-2 related genes, where analyzed, have distinct patterns of expression and thus may function in different tissues. The cell death program is in place in all tissues and may be regulated by different Bcl-2 related genes. While Bcl-2 expression is required for maintenance of the mature immune system, it is desirable to identify other genes which may govern apoptotic cell death in other lineages. From the perspective of pharmaceutical development, it would be desirable to identify or develop agents that either activate or suppress apoptosis, depending on the clinical setting.

SUMMARY OF THE INVENTION

The present inventor has surprisingly discovered a novel composition of matter which has been isolated and characterized, and which is described in a number of embodiments herein. Referred to herein as "Bbk," it appears to be a member of the Bcl-2 family, and can, inter alia, induce apoptosis in cells and oppose the function of Bcl-2 and related cell death suppresors in cells. Isolation of a full length human Bbk cDNA revealed that the deduced Bbk amino acid sequence shares homology with Bcl-2. Bbk mRNA appears to be widely expressed in primary human tissues. Bbk is an important regulator of apoptosis in human tissues and/or tumor cells.

Expression of Bbk accelerates apoptosis when expressed in normal rat fibroblasts (Rat1), and in human tumor cell lines including HeLa and BT549 cells. The co-expression of Bak and Bbk in Rat 1 cells does not block the induction of apoptosis, suggesting that their ability to bind each other does not inhibit their ability to promote apoptosis. Their coexpression may result in cooperative induction of cell death. The apoptotic function of Bbk can be reversed by the coexpression of the known survival proteins, Bcl-2, Bcl-$x_L$ and Epstein-Barr virus BHRF 1. Increasing the ratio of Bbk relative to the survival proteins may restore apoptosis as has been previously shown with the apoptosis promoting protein Bik.

The present invention thus relates to an apoptosis associated protein Bbk, products and processes involved in the cloning, preparation and expression of genes for Bbk; antibodies with specificity to Bbk; and nucleotide probes corresponding to the Bbk nucleotide sequence or portions thereof. The Bbk polypeptide is useful for producing antibodies thereto. The antibodies and probes are useful for detecting and isolating Bbk in biological specimens including for example, cells from all human tissues including heart tissue, lung tissue, tumor cells, placenta, liver, skeletal muscle, kidney, and pancreas.

The present invention further relates to species homologs and viral homologs of Bbk.

The present invention relates to the identification, characterization and sequencing of cDNAs and genomic fragments which encode the Bbk that is present in human cells.

According to the present invention, there are provided genetic sequences encoding Bbk. The instant invention also provides for expression vectors containing such genetic sequences, hosts transformed with such expression vectors, and methods for producing the genetically engineered or recombinant Bbk.

The present invention also provides antibodies which specifically recognize Bbk.

The Bbk cDNA and recombinant protein are useful for making antibodies which specifically recognize Bbk. Such antibodies are useful for detecting and isolating Bbk in a biological specimen. The present Bbk protein is also useful as a regulator of apoptosis.

A small cDNA from an EBV-transformed B-cell line has been isolated. The amino acid sequence of the Bbk protein shares sequence homology with Bcl-2 domains.

The present invention further relates to a method for isolating Bbk partial clones using polymerase chain reaction (PCR) cloning, from diverse human tumor cell lines.

The present invention is further directed to methods for inducing or suppressing apoptosis in individuals suffering from degenerative disorders characterized by inappropriate cell proliferation or inappropriate cell death, respectively. Degenerative disorders characterized by inappropriate cell proliferation include, for example, inflammatory conditions, cancer, including lymphomas, genotypic tumors, etc. Degenerative disorders characterized by inappropriate cell death include, for example, autoimmune diseases, acquired immunodeficiency disease (AIDS), cell death due to radiation therapy or chemotherapy, etc.

The present invention also relates to methods for detecting the presence of Bbk protein, as well as methods directed to the diagnosis of degenerative disorders, which disorders are associated with an increased or decreased level of expression or mutations of Bbk, as compared to the expected level of Bbk expression in the normal cell population.

The present invention is further directed to methods for monitoring the progress of degenerative disorders associated with increased or decreased levels of expression of Bbk, by monitoring Bbk expression.

The present invention also relates to methods for determining whether a disease/degenerative disorder is linked to abnormal Bbk expression, as well as methods for determining the effect of over-expression or loss of expression of Bbk in animal models such as transgenic mice and/or homozygous null mice. Methods for determining whether a disease/ degenerative disorder is linked to abnormal Bbk expression include analyzing Bbk expression in diseased tissue as compared to normal tissue by for example, Northern and/or Western blots, as well as by other assay methods readily chosen and employed by those of ordinary skill in the art.

The present invention relates to hybrids of Bbk for therapeutic use.

The present invention also relates to methods for modulating apoptotic effects by administering the present Bbk protein, mutant protein or hybrids to an individual suffering from a degenerative disorder characterized by inappropriate cell proliferation or inappropriate cell death in order to stabilize inappropriate cell proliferation (i.e., induce apoptosis) or stabilize inappropriate cell death (i.e., suppress apoptosis), respectively, and/or in either case to restore normal cell behavior. FIG. 3 illustrates levels of Bbk mRNA expressed in a variety of healthy fetal and adult tissues.

The present invention further relates to functional equivalents including functional fragments of Bbk including, for example, peptides of Bbk such as BH1 and BH2, and other regions of homology recognized by the present inventor between Bbk and other apoptosis related proteins including Bcl-2 and Bax.

In a particular aspect, the invention is directed to a novel protein domain which has been identified and mapped to a short subsequence in the central portion of the Bbk molecule. This novel protein domain, which the inventor has designated the "Bbk BH3 domain," is essential both to Bbk's interaction with Bak, and to Bbk's cell killing function. Truncated Bbk species encompassing the Bbk BH3 domain are themselves sufficient to kill cells in transfection assays.

The Bbk BH3 domain shares less than twenty-five percent identity with the GD Domain first described in Bak in U.S. application Ser. No. 08/440,391, filed 12 May, 1995, U.S. Pat. No. 5,656,725 (BH3 is referred to therein as the GD domain). However, as observed with respect to the GD Domain in Bak, mutation of Bbk BH3 domain elements in Bbk diminishes cell killing and protein binding function. Thus, the Bbk BH3 domain is responsible for mediating key protein/protein interactions of significance to the actions of multiple cell death regulatory molecules.

In one aspect, then, the invention is directed to purified and isolated peptides comprising the Bbk BH3 domain and to molecules that mimic its structure and/or function, useful for inducing or modulating the apoptotic state of a cell. Chemical compounds that disrupt the function of the Bbk BH3 domain have utility as apoptosis-modulating agents. Accordingly, in another aspect, the invention is directed to agents capable of disrupting Bbk BH3 domain function. Such agents include, but are not limited to, molecules that bind to the Bbk BH3 domain, molecules that interfere with the interaction of the Bbk BH3 domain with other protein(s), and molecules comprising the Bbk BH3 domain which is altered in some manner. The invention provides methods to identify molecules that modulate apoptosis by disrupting the function of the Bbk BH3 domain, which accordingly comprise additional contemplated embodiments.

In additional aspects, the present invention relates to products and processes involved in the cloning, preparation and expression of peptides comprising the Bbk BH3 domain; antibodies with specificity to the Bbk BH3 domain; and nucleotide sequences encoding the Bbk BH3 domain or portions thereof. Peptides comprising the Bbk BH3 domain are useful for producing antibodies thereto. Such antibodies are useful for detecting and isolating proteins comprising the Bbk BH3 domain in biological specimens including, for example, cells from all human tissues including heart tissue, lung tissue, tumor cells, brain tissue, placenta, liver, skeletal muscle, kidney, and pancreas, as well as for modulating the apoptotic activity of proteins comprising the Bbk BH3 domain in and from such biological specimens, and constitute additional aspects of the invention.

In yet another aspect, the invention provides for expression vectors containing genetic sequences, hosts transformed with such expression vectors, and methods for producing the recombinant Bbk BH3 domain peptides of the invention.

The present invention is further directed to methods for inducing or suppressing apoptosis in the cells and/or tissues of individuals suffering from degenerative disorders characterized by inappropriate cell proliferation or inappropriate cell death, respectively. Degenerative disorders characterized by inappropriate cell proliferation include, for example, inflammatory conditions, cancer, including lymphomas, such as prostate hyperplasia, genotypic tumors, etc. Degenerative disorders characterized by inappropriate cell death include, for example, autoimmune diseases, acquired immunodeficiency disease (AIDS), cell death due to radiation therapy or chemotherapy, neurodegenerative diseases, such as Alzheimer's disease and Parkinson's disease, etc.

The present invention also relates to methods for detecting the presence of the Bbk BH3 domain peptide, as well as methods directed to the diagnosis of degenerative disorders, which disorders are associated with an increased or decreased level of expression of proteins comprising the Bbk BH3 domain, as compared to the expected level of expression of such proteins in the normal cell population.

The present invention relates to the therapeutic use of peptides comprising the Bbk BH3 domain.

The present invention also relates to methods for modulating the apoptotic state of a cell by administering peptides comprising the Bbk BH3 domain peptide, or mutants thereof, to an individual suffering from a degenerative disorder characterized by inappropriate cell proliferation or inappropriate cell death, in order to stabilize inappropriate cell proliferation (i.e., induce apoptosis) or stabilize inappropriate cell death (i.e., suppress apoptosis), respectively, and/or in either case to restore normal cell behavior.

The present invention is also directed to nucleotide probes which can be used to determine the presence of Bbk as well as to identify and isolate homologs including species homologs and viral homologs.

These and other objects and aspects of the invention will be apparent to those of skill from the description which follows.

DESCRIPTION OF THE FIGURES

FIGS. 1A–1C. Features of the yeast two-hybrid system (adapted from Clontech manual).

FIG. 1(A). A schematic illustration of the yeast GAL4 protein showing the DNA binding domain (bd) that interacts with the GAL1 upstream activating sequence (UAS) and the transcription activation domain (ad) that stimulates transcription.

FIG. 1(B). The GAL4 bd fused to protein X can bind to the GAL1 UAS but cannot stimulate transcription due to the lack of an activation domain. The GAL4 ad fused to protein Y also fails to stimulate transcription due to failure to localize to the promoter.

FIG. 1(C). The interaction of GAL4 bd/protein X fusion with the GAL1 UAS and its additional interaction with the GAL4 ad/protein Y fusion allows the reconstitution of GAL4 function and the stimulation of transcription.

FIG. 2. The nucleotide sequence and putative open reading frame (ORF) of clone Bbk [SEQ ID NOS:9–11] Arrows indicate the start points of several related clones also isolated by the two-hybrid analysis. The position of an AAG insert identified in several clones is also indicated.

FIG. 4(A). In vitro translation of $^{35}$S-labeled Bbk in rabbit reticulocyte lysate. Controls include translation of luciferase protein was resolved by SDS gel electrophoresis and visualized by autoradiography. The gel mobilities of pre-stained protein molecular weight markers (Amersham) are shown.

FIG. 4(B). Expression of Bbk in transfected cells. Plasmids expressing the hemagglutinin (HA) epitope-tagged Bax or Bbk were transfected into COS7 cells. Lysates were prepared 48 hrs after transfection. Lysates of untransfected COS7 cells are included as a negative control. Proteins were detected by SDS gel electrophoresis and Western blot of cell lysates with the anti-HA monoclonal antibody 12CA5 (Boehringer Mannheim). The Bax and Bbk proteins are indicated with arrows.

FIG. 5(A). Effect of transient expression of vector (0.42 μg pRcCMV), Bak (0.21 μg pcDNA1/HABak+0.21 μg pRcCMV), Bbk (0.21 μg pcDNA3/HABbk+0.21 μg pRcCMV), or Bak+Bbk (0.21 μg pcDNA3/HABak+0.21 μg pcDNA3/HABbk) in Rat1 cells.

FIG. 5(B). Effect of the survival proteins Bcl-2 (0.21 μg pcDNA3/HABbk+0.21 μg pRcCMV/Bcl-2), Bcl-x$_L$ (0.21 μg pcDNA3/HABbk+0.21 μg pRcCMV/Bcl-x$_L$), or Epstein Barr virus BHRF1 (0.21 μg pcDNA3/HABbk+0.21 μg pRcCMV/BHRF1) upon Bbk induction of apoptosis in Rat1 cells.

FIG. 6(A). HeLa cells were transfected with pRcCMV/βgal (0.16 μg) plus vector (0.42 μg pRcCMV), Bak (0.21 μg pcDNA1/HABak+0.21 μg pRcvCMV), or Bbk (0.21 μg pcDNA3/HABbk+0.21 μg pRcCMV). Stained cells were scored and plotted as described in FIG. 5.

FIG. 6(B). BT549 cells were transfected as described in panel (A).

FIGS. 8A–8B. Sequence alignment of Bbk with Bcl-2 family member BH2 and BH3 domains.

FIG. 8(A). The BH2 domain sequences of Bak [SEQ ID NO:13], Bax [SEQ ID NO:14], Bik [SEQ ID NO:15], Bcl-2 [SEQ ID NO:16] and Bcl-x$_L$ [SEQ ID NO:17] are aligned with the homologous regions of Bbk [SEQ ID NO:12]. Residues that are identical or conservative in at least three of the proteins are boxed. Black boxes indicate identical residues while grey boxes indicate conservative residues. Numbering indicates the position of the first amino acid residue shown for each sequence.

FIG. 8(B). The BH3 domain sequences of Bak [SEQ ID NO:19], Bax [SEQ ID NO:20], Bik [SEQ ID NO:21], Bcl-2 [SEQ ID NO:22] and Bcl-x$_L$ [SEQ ID NO:233] are aligned with the homologous regions of Bbk [SEQ ID NO:18]. Shading and numbering are as described in panel (A).

FIGS. 9A–9C. Deletion and point mutation analysis of Bbk in Rat1 cells.

FIG. 9(A). Rat1 cells were transfected with pRcCMV/βgal (0.16 μg) plus vector (0.42 μg pRcCMV), full length Bbk (0.42 μg pcDNA3/HABbk), or deletion mutants of Bbk (0.42 μg pcDNA3/HAΔ1–105 or 0.42 μg pcDNA3/HAΔ142–249). Stained cells were scored and plotted as described in FIG. 5.

FIG. 9(B). Alanine point mutants of the Bbk BH3 domain (PM-LVLEE [SEQ ID NO:25], PM-V [SEQ ID NO:26], PM-L [SEQ ID NO:27], PM-EE [SEC ID NO:28]) are compared to the wild type Bbk BH3 domain [SEQ ID NO 24]. The shading is as described in FIG. 8 with Alanine substitutions indicated as outlined boxes.

FIG. 9(C). The alanine point mutants shown in panel (B) (0.42 μg each pcDNA3/HAPM-LVLEE, pcDNA3/HAPM-V, pcDNA3/HAPM-L, pcDNA3/HAPM-EE plus 0.16 μg pRcCMV/βgal) were transfected into Rat1 cells and compared to cells transfected with vector control plasmid or wild type Bbk as described in panel (A). Stained cells were scored and plotted as described in FIG. 5.

FIG. 10. Effect of Bbk BH3 domain expression on the viability of Rat1 cells. Rat1 cells were transfected with pRcCMV/bβgal (0.16 mg) plus vector (0.42 mg pRcCMV), full length Bbk (0.42 mg pRcCMV/HABbk), or Bbk BH3 domain (0.42 mg pRcCMV/HABbkBH3). Stained cells were scored and plotted as described in FIG. 5.

DETAILED DESCRIPTION OF THE INVENTION

Figure 1C:
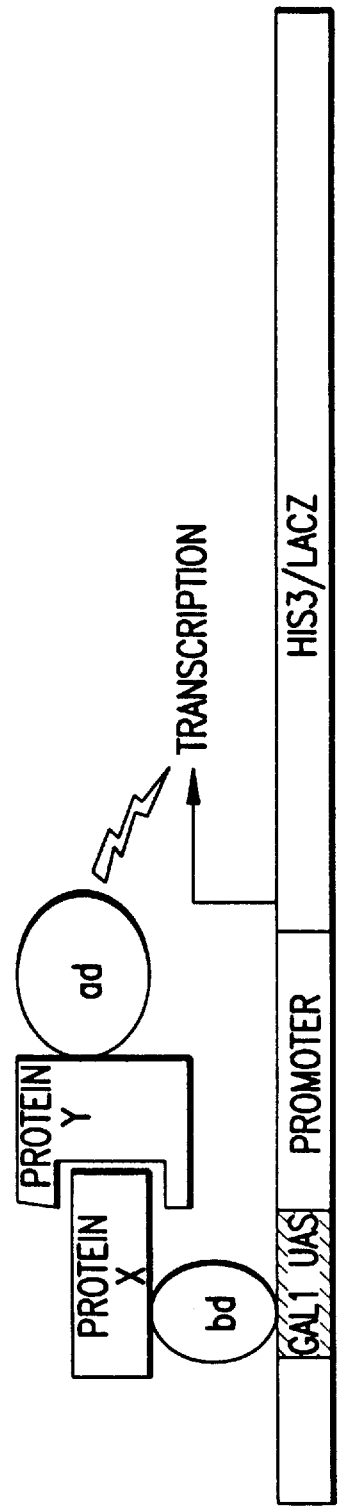

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. Standard reterence works setting forth the general principles of recombinant DNA technology include Sambrook, J., et al., *Molecular Cloning,: A Laboratory Manual*, 2d Ed., Cold Spring Harbor Laboratory Press, Planview, N.Y. (1989); McPherson, M. J., Ed., *Directed Mutagenesis: A Practical Approach*, IRL Press, Oxford (1991); Jones, J., *Amino Acid and Peptide Synthesis*, Oxford Science Publications, Oxford (1992); Austen, B. M. and Westwood, O. M. R., *Protein Targeting and Secretion*, IRL Press, Oxford (1991). Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted.

This invention is directed most generally to a novel protein designated "Bak binding killer" protein or "Bbk" based upon its ability to bind specifically to the protein Bak and to kill immortalized human tumor cells. Accordingly, this invention comprises amino acid sequences of Bbk or Bbk mutants, genetic sequences coding for such amino acid sequences, expression vehicles containing the genetic sequences, hosts transformed therewith and recombinant Bbk and antisense RNA produced by such transformed host expression. The invention further comprises antibodies directed against Bbk and/or fragments thereof or against Bbk mutants.

The process for genetically engineering such protein sequences, according to the invention, is facilitated through the cloning of genetic sequences which are capable of encoding the peptide and through the expression of such genetic sequences. As used herein, the term "genetic sequences" is intended to refer to a nucleic acid molecule (preferably DNA). Genetic sequences which are capable of encoding the proteins are derived from a variety of sources. These sources include genomic DNA, cDNA, synthetic DNA, and combinations thereof. The preferred source of the genomic DNA or mRNA is human tissue including heart, lung, tumor cells, placenta, liver, skeletal muscle, and pancreas. The mRNA may then be used to obtain cDNA by techniques known to those skilled in the art. Probes may be synthesized based on the nucleotide sequence of Bbk by methods known in the art.

The Bbk protein or fragment genomic DNA of the invention may or may not include naturally occurring introns. Moreover, such genomic DNA may be obtained in association with the 5' promoter region of the Bbk protein gene sequences and/or with the 3' transcriptional termination region. Further, such genomic DNA may be obtained in association with the genetic sequences which encode the 5' non-translated region of the Bbk protein mRNA and/or with the genetic sequences which encode the 3' non-translated region. To the extent that a host cell can recognize the transcriptional and/or translational regulatory signals associated with the expression of the mRNA and protein, the 5' and/or 3' non-transcribed regions of the native gene, and/or the 5' and/or 3' non-translated regions of the mRNA, may be retained and employed for transcriptional and translational regulation. Bbk protein genomic DNA can be extracted and purified from human tissue by means well known in the art (for example, see Berger, S. L., et al., Eds., *Guide to Molecular Cloning Techniques*, Academic Press (1987)).

Alternatively mRNA can be isolated from any cell which produces or expresses the protein, and used to produce cDNA by means well known in the art (for example, see Berger, S. L., et al., Eds., *Guide to Molecular Cloning Techniques*, Academic Press (1987)). Preferably, the mRNA preparation used will be enriched in mRNA coding for such Bbk protein, either naturally, by isolation from cells which are producing large amounts of the protein, or in vitro, by techniques commonly used to enrich mRNA preparations of specific sequences, including for example sucrose gradient centrifugation, or PCR. cDNA can then be prepared for example, by reverse transcription. The cDNA can then be amplified by PCR using suitable primers.

For cloning into a vector, such suitable DNA preparations (either human genomic DNA or cDNA) are randomly sheared or enzymatically cleaved, respectively, and ligated into appropriate vectors to form a recombinant gene (either genomic or cDNA) library. A DNA sequence encoding the Bbk protein or its functional equivalents may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, for example, by Sambrook, J., et al., *Molecular Cloning: A Laboratory Manual*, 2d Ed., Cold Spring Harbor Laboratory Press, Planview, N.Y. (1989), and are well known in the art.

Libraries containing the Bbk protein clones may be screened and a Bbk clone identified by any means which specifically selects for Bbk protein DNA such as, for example, (a) by hybridization with an appropriate nucleic acid probe(s) containing a sequence specific for the DNA of this protein, or (b) by hybridization-selected translational analysis in which native mRNA which hybridizes to the clone in question is translated in vitro and the translation products are further characterized, or, (c) if the cloned genetic sequences are themselves capable of expressing mRNA, by immunoprecipitation of a translated Bbk or fragment product produced by the host containing the clone.

Oligonucleotide probes specific for the protein which can be used to identify clones to this protein can be designed from knowledge of the amino acid sequence of the Bbk protein. The sequence of amino acid residues in a peptide is designated herein either through the use of their commonly employed three-letter designations or by their single-letter designations. A listing of these three-letter and one-letter designations may be tound in textbooks such as *Biochemistry*, 2ed., Lehninger, A., Worth Publishers, New York, N.Y. (1975). When the amino acid sequence is listed horizontally, the amino terminus is intended to be on the left end whereas the caiboxy terminus is intended to be at the right end. The residues of amino acids in a peptide may be separated by hyphens. Such hyphens are intended solely to facilitate the presentation of a sequence.

Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., In: *Molecular Biology of the Gene*, 3rd Ed., W. A. Benjamin, Inc., Menlo Park, Calif. (1977)), one or more different oligonucleotides can be identified from the amino acid sequence, each of which would he capable of encoding the present Bbk or fragment protein. The probability that a particular oligonucleotide will, in fact, constitute the actual protein coding sequence can be estimated by considering abnormal base pairing relationships and the frequency with which a particular codon is actually used (to encode a particular amino acid) in eukaryotic cells. Such "codon usage rules" are disclosed by Lathe, et al., *J. Molec. Biol.* 183:1–12 (1985). Using the "codon usage rules" of Lathe, a single oligonucleotide sequence, or a set of oligonucleotide sequences, that contains a theoretical "most probable" nucleotide sequence capable of encoding the Bbk protein sequences is identified.

The suitable oligonucleotide, or set of oligonucleotides, which is capable of encoding a fragment of the Bbk protein gene (or which is complementary to such an oligonucleotide, or set of oligonucleotides) may be synthesized by means well known in the art (see, for example, S. A. Narang, Ed., *Synthesis and Application of DNA and RNA*, Academic Press, San Diego, Calif.) and employed as a probe to identify and isolate the cloned Bbk protein gene by techniques known in the art. Techniques of nucleic acid hybridization and clone identification are disclosed by Maniatis, et al., Eds., *Molecular Cloning, A Laboratory Manual*, Cold Spring Harbor Laboratories, Cold Spring Harbor, N.Y., (1982); Berger, et al., Eds., *Guide to Molecular Cloning Techniques*, Academic Press, San Diego, Calif., (1988); Sambrook, J., et al., *Molecular Cloning: A Laboratory Manual*, 2d Ed., Cold Spring Harbor Laboratory Press, Planview, N.Y. (1989); and by Hames, et al., Eds., *Nucleic Acid Hybridization, A Practical Approach*, IRL Press, Washington, D.C., (1985), which references are herein incorporated by reference. Those members of the above-described gene library which are found to be capable of such hybridization are then analyzed to determine the extent and nature of the Bbk protein encoding sequences which they contain.

To facilitate the detection of the desired Bbk or fragment protein DNA encoding sequence, the above-described DNA probe is labeled with a detectable group or label. Such detectable group or label can be any material having a detectable physical or chemical property. Such materials have been well-developed in the field of nucleic acid hybridization and in general most any label useful in such methods can be applied to the present invention. Particularly useful are radioactive labels, such as $^{32}$P, $^{3}$H, $^{14}$C, $^{35}$S, $^{125}$I or the like. Any radioactive label may be employed which provides for an adequate signal and has a sufficient half-life. The oligonucleotide may be radioactively labeled, for example, by "nick-translation" by well-known means, as described in, for example, Rigby, et al., *J. Mol Biol.* 113:237 (1977) and by T4 DNA polymerase replacement synthesis as described in, for example, Deen, et al., *Anal. Biochem.* 135:456 (1983).

Alternatively, polynucleotides are also useful as nucleic acid hybridization probes when labeled with a non-radioactive marker such as biotin, an enzyme or a fluorescent or chemiluminescent group. See, for example, Leary, et al., *Proc. Natl. Acad. Sci, USA* 80:4045 (1983); Renz, et al., *Nucl. Acids Res.* 12:3435 (1984); and Renz, M., *EMBO J.* 6:817 (1983).

Thus, the actual identification of the Bbk protein sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the Bbk protein gene.

In an alternative way of cloning the Bbk protein gene, a library is prepared using an expression vector, by cloning DNA or, more preferably, cDNA prepared from a cell capable of expressing the Bbk protein, into an expression vector. The library is then screened for members which express the Bbk protein, for example, by screening, the library with antibodies to the Bbk protein.

The above discussed methods arc, therefore, capable of identifying genetic sequences which are capable of encoding Bbk proteins or fragments thereof. In order to further characterize such genetic sequences, and, in order to produce the recombinant protein, it is desirable to express the proteins which these sequences encode. Such expression identities those clones which express proteins possessing characteristics of the Bbk proteins. Such characteristics may include the ability to specifically bind antibody to the Bbk protein and the ability to elicit the production of an antibody or antibodies which are capable of binding to the Bbk protein.

To express the Bbk protein or a functional equivalent, or mutant thereof, transcriptional and translational signals recognizable by an appropriate host are necessary. The cloned Bbk encoding sequences, obtained, for example, through the methods described above, and preferably in a double-stranded form, may be operably linked to sequences controlling transcriptional expression in an expression vector, and introduced into a host cell, either prokaryotic or eukaryotic, to produce recombinant Bbk protein or a functional equivalent thereof. Depending upon which strand of the Bbk encoding sequence is operably linked to the sequences controlling transcriptional expression, it is also possible to express Bbk antisense RNA or a functional equivalent thereof.

Expression of Bbk in different hosts may result in different post-translational modifications which may alter the properties of the Bbk. The present invention encompasses the expression of the Bbk protein, or functional equivalent thereof, or Bbk mutant, in prokaryotic or eukaryotic cells, and particularly, eukaryotic expression is preferred.

Preferred prokaryotic hosts include bacteria such as *E. coli*, Bacillus, Streptomyces, Pseudomonas, Salmonella, Serratia, etc. The most preferred prokaryotic host is *E. coli*. Other enterobacteria such as *Salmonella typhimurium* or *Serratia marcescens*, and various Pseudomonas species may also he utilized. Under such conditions, the protein may not be glycosylated. The prokaryotic host must be compatible with the replicon and control sequences in the expression plasmid.

To express the Bbk protein (or a functional equivalent thereof) or Bbk mutant in a prokaryotic cell (such as, for example, *E. coli, B. subtilis*, Pseudomonas, Streptomices, etc.), it is necessary to operably link the Bbk encoding sequence to a functional prokaryotic promoter. Such promoters may be either constitutive or, more preferably, regulatable (i.e., inducible or derepressible). Examples of constitutive promoters include the int promoter of bacteriophage lambda, the bla promoter of the β-lactamase gene of pBR322, and the CAT promoter of the chloramphenicol acetyl transferase gene of pBR325, etc. Examples of inducible prokaryotic promoters include the major right and left promoters of bacteriophage lambda ($P_L$ and $P_R$), the trp, recA, lacZ, lacI, and gal promoters of E. coli, the α-amylase (Ulmanen, I., et al., J. Bacterial. 162:176–182 (1985)) and the sigma-28-specific promoters of B. subtilis (Gilman, M. Z., et al., Gene 32:11–20 (1984)), the promoters of the bacteriophages of Bacillus (Gryczan, T. J., The Molecular Bioloty of the Bacilli, Academic Press, Inc., N.Y. (1982)), and Streptomyces promoters (Ward, J. M., et al., Mol. Gen. Genet. 203:468–478 (1986)). Prokaryotic promoters are reviewed by Glick, B. R., (J. Ind. Microbial. 1:277–282 (1987)); Cenatiempo, Y. (Biochimie 68:505–516 (1986)); and Gottesman, S. (Ann. Rev. Genet. 18:415–442 (1984)).

Proper expression in a prokaryotic cell also requires the presence of a ribosome binding site upstream of the gene-encoding sequence. Such ribosome binding sites are disclosed, for example, by Gold, L., et al. (Ann. Rev. Microbial. 35:365–404 (1981)).

Especially preferred eukaryotic hosts include mammalian cells either in vivo, in animals or in tissue culture. General principles of mammalian cell culture are known in the art and are described, for example, in Butler, M. and Dawson, M., Eds., Cell Culture LabFax, Bios Scientific Publishers Ltd., Oxford, UK and Academic Press, Inc., San Diego, Calif., Publishers (1992), and references cited therein.

Expression of the Bbk in eukaryotic hosts requires the use of regulatory regions functional in such hosts, and preferably eukaryotic regulatory systems. A wide variety of transcriptional and translational regulatory sequences can be employed, depending upon the nature of the eukaryotic host. The transcriptional and translational regulatory signals can also be derived from the genomic sequences of viruses which intect eukaryotic cells, such as adenovirus, bovine papilloma virus, Simian virus, herpes virus, or the like. Preferably, these regulatory signals are associated with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA product capable of translation are preferred, and especially, strong promoters such as the promoter for actin, collagen, myosin, etc., can be employed provided they also function as promoters in the host cell. Preferred eukaryotic promoters include the promoter of the mouse metallothionein I gene (Hamer, et al., J. Mol. Appl. Gen. 1:273–288 (1982)); the TK promoter of Herpes virus (McKnight, S., Cell 31:355–365 (1982)); the SV40 early promoter (Benoist, et al., Nature (London) 290:304–310 (1981)); and the HCMV promoter (Boshart, et al., Cell 41:521 (1985)); in yeast, the yeast gal4 gene promoter (Johnston, et al., Proc. Natl. Acad. Sci. USA 79:6971–6975 (1982); Silver, et al., Proc. Natl. Acad. Sci. USA 81:5951–5955 (1984)) or a glycolytic gene promoter may be used.

As is widely known, translation of eukaiyotic mRNA is initiated at the codon which encodes the first methionine. For this reason, it is preferable to ensure that the linkage between a eukaryotic promoter and a DNA sequence which encodes the Bbk protein, or a functional equivalent thereof does not contain any intervening codons which are capable of encoding a methionine. The presence of such codons results either in the formation of a fusion protein (if the AUG codon is in the same reading frame as the Bbk encoding DNA sequence) or a frame-shift mutation (if the AUG codon is not in the same reading frame as the Bbk encoding sequence).

If desired, a fusion product of the Bbk may be constructed. For example, the sequence coding for the Bbk or fragment thereof may be liked to a signal sequence which will allow secretion of the protein from or the compartmentalization of the protein in, a particular host. Such signal sequences may be designed with or without specific protease sites such that the signal peptide sequence is amenable to subsequent removal.

Transcriptional initiation regulatory signals can be selected which allow for repression or activation, so that expression of the operably linked genes can he modulated. Of interest are regulatory signals which are temperature-sensitive, such that by varying the temperature, expression can be repressed or initiated, or which are subject to chemical regulation, e.g., by a metabolite. Also of interest are constructs wherein the Bbk mRNA and antisense RNA are provided in a transcribable form, but with different promoters or other transcriptional regulatory elements such that induction of Bbk mRNA expression is accompanied by repression of antisense RNA expression, and/or repression of Bbk mRNA expression is accompanied by induction of antisense RNA expression.

Translational signals are not necessary when it is desired to express Bbk antisense RNA sequences.

If desired, the non-transcribed and/or non-translated regions 3' to the sequence coding for the Bbk protein can be obtained by the above-described cloning methods. The 3'-non-transcribed region may be retained for its transcriptional termination regulatory sequence elements; the 3'-non-translated region may be retained for its translation termination regulatory sequence elements, or for those elements which direct polyadenylation in eukaryotic cells. Where the native expression control sequence signals do not function satisfactorily in the host cell, then sequences functional in the host cell may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert the Bbk DNA construct into the host cell chromosomal DNA, or to allow it to exist in an extrachromosomal form.

If the bbk DNA encoding sequence and an operably linked promoter are introduced into a recipient eukaryotic cell as a non- replicating DNA (or RNA) molecule, which may either be a linear molecule or a closed covalent circular molecule which is incapable of autonomous replication, then the expression of the Bbk protein may occur through the transient expression of the introduced sequence.

Genetically stable transformants may be constructed with vector systems, or transformation systems, whereby bak DNA is integrated into the host chromosome. Such integration may occur de novo within the cell or, in a preferred embodiment, be assisted by transformation with a vector which functionally inserts itself into the host chromosome, for example, with retroviral vectors, transposons or other DNA elements which promote integration of DNA sequences into chromosomes. A vector is employed which is capable of integrating the desired gene sequences into a mammalian host cell chromosome.

Cells which have stably integrated the introduced DNA into their chromosomes are selected by also introducing one or more markers which allow for selection of host cells which contain the expression vector in the chromosome, for example, the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the case with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein, et al., *Miami Wntr. Symp.* 19:265–274 (1982); Broach, J. R., *The Molecular Biology of the Yeast Saccharomyces: Life Cycle and Inheritance*, Cold Spring Harbor Laboratory, Cold Spring Harbor, N.Y., pp. 445–470 (1981); Broach, J. R., *Cell* 28:203–204 (1982); Bollon, et sl., *J. Clin, Hematol. Oncol.* 10:39–48 (1980); Maniatis, T., "Gene Expression," In: *Cell Biology: A Comprehensive Treatise*, Vol. 3, Academic Press, New York, pp. 563–608 (1980)), and are commercially available. For example, mammalian expression vector systems which utilize the MSV-LTR promoter to drive expression of the cloned gene, and in which it is possible to contransfect with a helper virus to amplify plasmid copy number, and integrate the plasmid into the chromosomes of host cells, have been described (Perkins, et al., *Mol. Cell Biol.* 3:1123 (1983); Clontech, Palo Alto, Calif.).

Once the vector or DNA sequence containing the construct(s) is prepared for expression, the DNA construct (s) is introduced into an appropriate host cell by any of a variety of suitable means, including transfection. After the introduction of the vector, recipient cells are grown in a selective medium, which selects for the growth of vector-containing cells. Expression of the cloned gene sequence(s) results in the production of the Bbk protein, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like).

The expressed protein is isolated and purified in accordance with conventional conditions, such as extraction, precipitation, chromatography, affinity chromatography, electrophoresis, or the like.

Bbk can he purified by growing the transformed host cells under suitable conditions which are well known in the art, the cells can be harvested and disrupted to extract total cellular protein. The protein can then, for example, be placed on a sizing column such as sepharose or agarose beads, and proteins of the correct molecular weight can be collected. The predicted molecular weight of Bbk is 26.7 kD and it runs with an apparent molecular weight of approximately 37 kD on SDS polyacrylamide gels.

Further purification can be effected by use of an anti-Bbk antibody. Such an antibody can be used to immunoprecipitate Bbk proteins from the set of cellular proteins of the correct approximate molecular weight. Such antibodies can, for example, be raised against polypeptides synthesized according to the sequence or subsequences of the sequence shown in FIG. 2. Alternatively, the antibodies can be raised against fusion proteins, which contain Bbk sequences as well as those of other proteins. After immunoprecipitation, the Bbk proteins can be released from the antibodies to provide a substantially pure preparation of Bbk protein.

The bbk DNA coding sequences, of the present invention may be used to obtain Bbk antisense RNA genetic sequences, inasmuch as the antisense RNA sequence will be that sequence found on the opposite strand of the strand transcribing the peptide core's mRNA. The antisense DNA strand may also be operably linked to a promoter in an expression vector such that transformation with this vector results in a host capable of expression of a Bbk antisense RNA in the transformed cell. Antisense RNA and its expression may be used to interact with an endogenous bbk DNA or RNA in a manner which inhibits or represses transcription or translation of the bbk genes in a highly specific manner. Use of antisense RNA probes to block gene expression is described, for example, in Lichtenstein, C., *Nature* 333:801–802 (1988).

Identification, Characterization and Use of Bbk Fragment Compositions Comprising the Bbk BH3 Domain A novel domain within the Bbk molecule that appears to be both necessary and sufficient for the known biological activities of Bbk has been identified. This domain, designated herein as the "Bbk BH3 domain," is sufficient to mediate cell killing function and may be sufficient for physical interaction with Bak. Mutation of Bbk BH3 domain sequences has been demonstrated to reduce the apoptotic activity of the Bbk protein in Rat1 fibroblast cells. These experiments demonstrate that the Bbk BH3 domain is required for the cell killing and Bak binding activities of the Bbk protein. These observations suggest that Bbk modulates or regulates apoptosis through a mechanism that involves the Bbk BH3 domain. As those of skill familiar with the present invention will appreciate, sequences comprising the Bbk BH3 domain are useful in modulating apoptosis in cells. Similarly, compounds and compositions which are capable ol binding to the Bbk BH3 domain are useful as agents for the modulation of apoptotic activity in cells.

As used herein, the term "Bbk BH3 domain" refers to a protein domain first identified in Bbk, demonstrated herein to be essential for the interaction of Bbk with Bak and for Bbk's cell killing function, and to peptides and/or molecules capable of mimicking its structure and/or function. In a preferred embodiment, the present invention comprises a peptide having the following amino acid sequence:

LRRLVALLEEEAE [SEQ ID NO:1]

corresponding to amino acid residues 125–137 of Bbk, as well as functional equivalents thereof. By "functional equivalent" is meant a peptide possessing a biological activity or immunological characteristic substantially similar to that of the Bbk BH3 domain, and is intended to include "fragments", "variants", "analogs", "homologs", or "chemical derivatives" possessing such activity or characteristic. Functional equivalents of the Bbk BH3 domain, then, may not share an identical amino acid sequence, and conservative or non-conservative amino acid substitutions of conventional or unconventional amino acids are possible.

Reference herein to "conservative" amino acid substitution is intended to mean the interchangeability of amino acid residues having similar side chains. For example, glycine, alanine, valine, leucine and isoleucine make up a group of amino acids having aliphatic side chains; serine and threonine are amino acids having aliphatic-hydroxyl side chains; asparagine and glutamine are amino acids having amide-containing side chains; phenylalanine, tyrosine and tryptophan are amino acids having aromatic side chains; lysine, arginine and histidine are amino acids having basic side chains; aspartic acid and glutamic acid are amino acids having acidic side chains; and cysteine and methionine are amino acids having sulfur-containing side chains. Interchanging one amino acid from a given group with another amino acid from that same group would be considered a conservative substitution. Preferred conservative substitution groups include asparagine-glutamine, alanine-valine, lysine-arginine, phenylalanine-tyrosine and valine-leucine-isoleucine.

In additional embodiments of the invention, there are provided peptides having the following amino acid sequence:

LRRLAALLEEEAE [SEQ ID NO:2]
LRRLVALAEEEAE [SEQ ID NO:3]
LRRLVALLEAAAE [SEQ ID NO:4]

corresponding to alanine point mutants as shown in FIG. 9, which also demonstrate significant Bbk cell killing function. The Bbk BH3 domain disclosed herein is uniquely involved in both cell killing and Bak binding activity of Bbk.

The functional importance of the Bbk BH3 domain is likely to be related to its ability to mediate one or more protein/protein interactions with other Bcl-2 family members, or with other as yet unidentified cellular protein (s). The present inventor does not intend to be bound by a particular theory; however, regardless of its mechanism(s) of action, the Bbk BH3 domain in Bbk is of central importance for mediating these protein/protein interactions.

Agents capable of modulating Bbk BH3 domain mediated protein/protein interactions may include peptides comprising the Bbk BH3 domain, as well as mutants of the Bbk BH3 domain or of proteins comprising the Bbk BH3 domain. A "mutant" as used herein refers to a peptide having an amino acid sequence which dilters from that of the naturally occurring peptide or protein by at least one amino acid. Mutants may have the same biological and immunological activity as the naturally occurring Bbk BH3 domain peptide or the naturally occurring protein. However, the biological or immunological activity of mutants may differ or be lacking. For example, a Bbk BH3 domain mutant may lack the biological activity which characterizes naturally occurring Bbk BH3 domain peptide, but may be useful as an antigen for raising antibodies against the Bbk BH3 domain or for the detection or purification of antibodies against the Bbk BH3 domain, or as an agonist (competitive or non-competitive), antagonist, or partial agonist of the function of the naturally occurring Bbk BH3 domain peptide.

Modulation of Bbk BH3 domain mediated protein/protein interactions may be effected by agonists or antagonists of Bbk BH3 domain peptides as well. Screening of peptide libraries, compound libraries and other information banks to identify agonists or antagonists of the function of proteins comprising the Bbk BH3 domain is accomplished with assays for detecting the ability of potential agonists or antagonists to inhibit or augment Bbk BH3 domain binding, e.g., Bbk BH3 domain homodimerization or heterodimerization.

For example, high through-put screening assays may be used to identify compounds that modulate the protein binding function of the Bbk BH3 domain. Such screening assays facilitate the identification of compounds that accelerate or inhibit apoptosis by influencing protein/protein interactions mediated by the Bbk BH3 domain. For example, an in vitro screen for compounds that disrupt the Bbk BH3 domain interaction with Bak comprises multiwell plates coated with Bak which are incubated with a labeled Bbk BH3 domain peptide probe in the presence of one or more compounds to be tested. Molecules that specifically disrupt the interaction could, in principle, bind to either the Bbk BH3 domain "ligand" or to the "receptor" domain in Bak. Either class of compound would be a candidate apoptosis-modulating agent.

Thus, the invention provides a method of screening for an agent capable of modulating apoptosis which comprises coating a multiwell plate with Bak and incubating the coated multiwell plate with a labeled Bbk BH3 domain peptide probe in the presence of an agent which it is desired to test, wherein disruption of Bbk BH3 domain interaction with Bak indicates that said agent is capable of modulating apoptosis. Agents identified by this method are also contemplated embodiments of the invention.

Suitable labels include a detectable label such as an enzyme, radioactive isotope, fluorescent compound, chemiluminescent compound, or bioluminescent compound. Those of ordinary skill in the art will know of other suitable labels or will he able to ascertain such using routine experimentation. Furthermore, the binding of these labels to the peptides is accomplished using standard techniques known in the art.

A high speed screen for agents that bind directly to the Bbk BH3 domain may employ immobilized or "tagged" combinatorial libraries. Agents that bind specifically to such libraries are candidates to be tested for their capacity to block Bbk/Bak interactions. As discussed above, such agents may function as suppressors of apoptosis by either directly inhibiting Bbk (and/or Bbk/Bak) function, or by increasing the effective activity of endogenous Bcl-2 (or other Bcl-2 family member). Such agents would be useful for suppressing aberrant apoptosis in degenerative disorders or following ischemic injury.

Antibodies against the Bbk BH3 domain peptides of the invention may be used to screen cDNA expression libraries for identifying clones containing cDNA inserts encoding structurally related, immunocrossreactive proteins which may be members of the Bbk BH3 domain family of proteins. Screening of cDNA and mRNA expression libraries is known in the art. Similarly, antibodies against Bbk BH3 domain peptides are used to identify or purify immunocrossreactive proteins related to this domain, or to detect or determnine the amount of proteins containing the Bbk BH3 domain in a cell or cell population, for example, in tissue or cells, such as lymphocytes, obtained from a patient. Known methods for such measurements include immunoprecipitation of cell extracts folllowed by PAGE, in sits detection by immunohistochemical methods, and ELISA methods, all of which are well known in the art.

Modulation of apoptosis according to the invention includes methods employing specific antisense polynucleotides complimentary to all or part of the nucleotide sequences encoding proteins comprising the Bbk BH3 domain disclosed herein. Such complimentary antisense polynucleotides may include nucleotide additions, deletions, substitutions and transpositions, providing that specific hybridization to the target sequence persists. Soluble antisense RNA or DNA oligonucleotides which can hybridize specifically to mRNA species encoding proteins comprising the Bbk BH3 domain, and which prevent transcription of the mRNA species and/or translation of the encoded polypeptide are contemplated as complimentary antisense polynucleotides according to the invention. Production of proteins comprising the Bbk BH3 domain is inhibited by antisense polynucleotides according to the invention, and such antisense polynucleotides may inhibit apoptosis, senescence and the like, tnd/or reverse the transformed phenotype of cells. A heterologous expression cassette maybe used to produce antisense polynucleotides in a transfectant or transgenic cell. Antisense polynucleotides also may be administered as soluble oligonucleotides to the external environment of the target cell, such as the culture medium of cells in vitro or the interstitial fluid (e.g., via the circulatory system) in vivo. Antisense polynucleotides and their use are known to those of skill, and are described, for example, in Melton, D. A., Ed, *Antisense RNA and DNA*, Cold Spring Harbor Laboratory Press, Cold Spring Harbor, N.Y. (1988).

The predicted biological activity of agents identified according to the invention varies depending on the assumptions made regarding the mechanism of Bbk/Bak function. For example, an agent which binds tightly to the Bbk BH3 domain would be predicted to inhibit Bbk (and perhaps Bbk/Bak) function. Assuming Bbk (and/or Bbk/Bak) is the active cell death regulatory molecule, an agent that binds tightly to the Bbk BH3 domain may inhibit Bbk function. Such agents might, therefore, exhibit anti-apoptotic activity under conditions in which Bbk has a demonstrated apoptotic effect. Agents in this class could have utility in treating diseases characterized by excessive or inappropriate cell death, including, for example, neuro-degenerative diseases and injury resulting from ischemia.

Peptidomimetics of Bbk BH3 domain peptide are also provided by the present invention, and can act as drugs for the modulation of apoptosis by, for example, blocking the function of proteins comprising the Bbk BH3 domain or interfering with Bbk BH3 domain mediated interations. Peptidomimetics are commonly understood in the pharmaceutical industry to include non-peptide drugs having properties analogous to those of those of the mimicked peptide. The principles and practices of peptidomimetic design are known in the art and are described, for example, in Fauchere J., *Adv. Drug Res.* 15: 29 (1986); and Evans et al., *J. Med. Chem.* 30:1229 (1987). Peptidomimetics which bear structural similarity to therapeutically useful peptides may be used to produce an equivalent therapeutic or prophylactic effect. Typically, such peptidomimetics have one or more peptide linkages optionally replaced by a linkage which may convert desirable properties such as resistance to chemical breakdown in vivo. Such linkages may include —$CH_2NH$—, —$CH_2S$—, —$CH_2$—$CH_2$—, —$CH$=$CH$—, —$COCH_2$—, —$CH(OH)CH_2$—, and —$CH_2SO$—. Peptidomimetics may exhibit enhanced pharmacological properties (biological half life, absorption rates, etc.), different specificity, increased stability, production economies, lessened antigenicity and the like which makes their use as therapeutics particularly desirable.

Immunization of animals with peptides comprising the Bbk BH3 domain alone or in conjunction with adjuvants by known methods can produce antibodies specific for the Bbk BH3 domain peptide. Antiserum obtained by conventional procedures may be utilized for this purpose. For example, a mammal, such as a rabbit, may be immunized with a peptide comprising the Bbk BH3 domain, thereby inducing the formation of polyclonal antibodies thereagainst. Monoclonal antibodies also may be generated using known procedures. Such antibodies can be used according to the invention to detect the presence and amount of peptides comprising the Bbk BH3 domain.

The Bbk BH3 domain peptides of the invention may be used for the detection of Bbk and other proteins by means of standard assays including radioimmunoassays and enzyme immunoassays.

It will be appreciated by those of skill that the precise chemical structure of peptides comprising the Bbk BH3 domain will vary depending upon a number of factors. For example, a given protein may be obtained as an acidic or basic salt, or in neutral form, since ionizable carboxyl and amino groups are found in the molecule. For the purposes of the invention, then, any form of the peptides comprising the Bbk BH3 domain which retains the therapeutic or diagnostic activity of the naturally occurring peptide is intended to be within the scope of the present invention.

The term "substantially homologous" as used herein refers to the ability of a first DNA sequence encoding Bbk to hybridize to a second DNA sequence encoding the foregoing, under stringent conditions, for example, at about 0.1x sodium citrate sodium chloride buffer (SSC) at a temperature of about 65° C. The term "substantially pure" means that the protein or molecule of interest is essentially free from any other detectable biological constituents. A "fragment" of a molecule such as Bbk is meant to refer to any variant of the molecule which possess the biological activity of the Bbk protein. A "variant" of a molecule is meant to refer to a molecule substantially similar in structure and biological activity or immunological characteristics to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or it the sequence of amino acid residues is not identical. An "analog" of a molecule is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties nmay alternatively decrease the toxicity of the molecule, eliminate or attenuate any undesirable side effect of the molecule, etc. Moieties capable of mediating such effects are described, for example, in Remington's Pharmaceutical Sciences (1980). Procedures for coupling such moieties to a molecule are well known in the art. By the term "modulate" is intended, for the purposes of the present invention, the induction of apoptosis by the administration of the Bbk protein of the invention, an active fragment thereof, a functional equivalent thereof, and/or the suppression or induction of apoptosis by the administration of a Bbk hybrid or Bbk mutant, or the administration of a vector containing cDNA encoding any of the foregoing, to the particular cells of an individual suffering from any degenerative disorder which results in inappropriate cell growth, for example, including lymphomas, genotypic tumors, cancer, or, disorders characterized by inappropriate cell death, for example, including AIDS which results in T-cell death, in order to stabilize inappropriate cell proliferation or inappropriate cell death and preferably to restore normal cell behavior.

By the term "administration" is intended any mode of administration which results in the delivery of the therapeutic agent across the cell membrane and into the desired cell. The site of administration and cells will be selected by one of ordinary skill in the art based upon an understanding of the particular degenerative disorder being treated. In addition, the dosage, dosage frequency, and length of course of treatment, can be determined and optimized by one of ordinary skill in the art depending upon the particular degenerative disorder being treated. The particular mode of administration can also be readily selected by one of ordinary skill in the art and can include, for example, oral, intravenous, subcutaneous, intramuscular, etc., with the requirement that the therapeutic agent cross the cell membrane. The therapeutic agent of the present invention can be the Bbk protein and/or functional equivalents thereof and/or Bbk hybrids or Bbk mutants and/or a vector containing CDNA encoding the foregoing. By the term "therapeutic agent" is intended the present Bbk protein, fragments, functional equivalents and/or hybrids or mutants thereof as well as vectors containing DNA encoding any of the foregoing. The present therapeutic agent can be administered alone or in combination with and/or concurrently with other suitable drugs and/or courses of therapy. By the term "degenerative disorder" is intended for purposes of this invention, any disorder characterized by inappropriate cell proliferation or inappropriate cell death or in some cases, both. By the term "inappropriate cell proliferation" is intended a statistically significant increase in cell number as compared to the proliferation of that particular cell type in the normal population. Also included are disorders whereby a cell is present and/or persists in an inappropriate location, e.g., the presence of fibroblasts in lung tissue after acute lung injury. For example, such cells include cancer cells which exhibit the properties of invasion and metastasis and are highly anaplastic. Such cells include but are not limited to, cancer cells including, for example, tumor cells. By the term "inappropriate cell death" is intended a statistically significant decrease in cell number as compared to the presence of that particular cell type in the normal population. Such underrepresentation may be due to a particular degenerative disorder, including, for example, AIDS (HIV), which results in the inappropriate death of T-cells, autoimmune diseases which are characterized by inappropriate cell death. By the term "autoimmune disease" is intended a disorder caused by an immune response directed against self antigens. Such diseases are characterized by the presence of circulating autoantibodies or cell-mediated immunity against autoantigens in conjunctions with inflammatory lesions caused by immunologically competent cells or immune complexes in tissues containing the autoantigens. Such diseases include systemic lupus erythematosus (SLE), rheumatoid arthritis.

By the term "suppression" is intended for the purposes of this invention the result achieved by administering an amount of a therapeutic agent containing Bbk hybrids or Bbk mutants thereof effective to suppress apoptosis in an individual suffering from a degenerative disorder characterized by inappropriate cell death. Suppression of apoptosis is achieved when the numbers of the particular affected cell type remain stable or increase in number to a level within the range observed in the normal cell population. By the term "stable" is intended the state achieved when a statistically significant decrease in cell number is no longer observed in the individual being treated, as compared to the cell number observed at the onset of the course of treatment. By the term "induction" is intended for the purposes of this invention the result achieved by the administration of an amount of a therapeutic agent containing the Bbk of the invention effective to induce apoptosis in cells of an individual ,suffering from a degenerative disorder characterized by inappropriate cell proliferation. The induction of apoptosis is achieved when cell numbers remain stable or decrease to a level within the range observed in the normal cell population. One of ordinary skill in the art can readily determine whether the induction of apoptosis has been achieved.

By the term "Bbk hybrid" is intended for the purposes of this invention, proteins which are hybrid proteins of the present Bbk proteins, fragments thereof, and/or functional equivalents or mutants thereof, with other apoptosis associated proteins encoded by genes including, for example, Bcl-2, Bax, c-myc, LMW5-HL, Bbk, Bcl-$X_L$, Bcl-$X_S$, BHRF-1, Mcl-1, A1 and ced9, fragments thereof and/or functional equivalents thereof, in order to produce a protein which exhibits enhanced, decreased, or intermediate apoptosis induction or suppression activity as compared to the activity of Bbk alone. Such hybrids can be produced, for example, by fusing the first half of the coding region of the bbk cDNA with the second half of the coding region of the cDNA for bcl-2, or bax, or bcl-$x_L$, or bcl-$x_S$ or vice versa. Additionally, by adding or replacing segments of bcl-2, bax, bcl-$x_L$ or bcl-$x_S$ to the bbk cDNA, chimeric gene products of therapeutic value can be generated. One of ordinary skill in the art can readily produce and employ such hybrids using techniques well known in the art. One of ordinary skill in the art can readily determine whether a particular hybrid exhibits enhanced, decreased or intermediate apoptosis induction or suppression activity using known screening methods and as described herein. By the term "normal cell behavior" is intended for the purposes of this invention, cells in which apoptosis proceeds normally. Normal cell behavior is observed in an organism which is able to remove senescent, damaged, or abnormal cells that could interfere with organ function or develop into tumors. Apoptosis which proceeds normally represents a coordinated cellular response to noxious stimuli that are not immediately lethal.

By the term "patient" or "individual" is intended for the purposes of the present invention, animals, including humans and mammals, who suffer from a degenerative disorder. By the term "Bbk mutant" is intended for the purposes of the present invention a mutant of Bbk which exhibits the reverse (apoptosis suppression) activity of the Bbk protein of the invention due to the substitution of one or more amino acids or corresponding nucleotides. By the term "apoptosis associated protein Bbk" is intended for the purposes of the present invention both the isolated naturally occurring and isolated recombinantly produced protein (i.e., synthetic Bbk) which exhibits, inter alia, apoptosis induction from human tissue including, for example, tumor cells and established human cell lines, and from tissues of other animals including mammals. This term includes any analog, homolog, mutant or derivative of isolated naturally occurring Bbk including fragments having less than the naturally occurring number of amino acids, such as partial fragments of natural or synthetic Bbk which retain the biological or immunological characteristics of the polypeptide disclosed in this application. This term also includes any peptide which contains the sequence of an isolated naturally occurring Bbk protein, or analog or homolog thereof, together with one or more flanking amino acids, which retains the biological or immunological characteristics of the Bbk protein of the invention.

Construction and Identification of Antibodies Raised Against Bbk, Functional Equivalents, Fragments, Hybrids, or Mutants Thereof In the following description, reference will be made to various methodologies well-known to those skilled in the art of immunology. Standard reference works setting forth the general principles of immunology include the work of Catty, D., *Antibodies. A Practical Approach*, Vol. 1, IRL Press, Washington, D.C. (1988); Klein, J., *Immunology: The Science of Cell-Noncell Discrimination*, John Wiley & Sons, New York (1982); Kennett, et al., *Monoclonal Antibodies. Hybridoma: A New Dimension in Biological Analyses*, Plenum Press, New York (1980); Campbell, A., "Monoclonal Antibody Technology," In: Burdon, R., et al., Eds., *Laboratory Techniques in Biochemistry and Molecular Biology*, Vol. 13, Elsevier, Amsterdam (1984); and Eisen, H. N., in: Davis, B. D., et al., Eds., *Microbiology*, 3d ed., Harper & Row, Philadelphia (1980).

An antibody is said to be "capable of binding" a molecule if it is capable of specifically reacting with the molecule to thereby bind the molecule to the antibody. The term "epitope" is meant to refer to that portion of a hapten which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evoked by other antigens.

The term "antibody" (Ab) or "monoclonal antibody" (Mib) as used herein is meant to include intact molecules as well as fragments thereof (such as, for example, Fab and F(ab)$_2$ fragments) which are capable of binding an antigen. Fab and F(ab)$_2$ fragments lack the Fc fragment of intact antibody, clear more rapidly from the circulation, and may have less non-specific tissue binding of an intact antibody (Wahl, et al., *J. NucL Med*. 24:16–325 (1983)).

The antibodies of the present invention have specificity to one or more epitopes present on the Bbk peptide, or an idiotype on the present Bbk. The antibodies of the invention can be polyclonal or monoclonal, provided that they are made with the present Bbk polypeptide or fragment thereof as the immunogen. Both of these types of antibodies can be utilized in the applications described herein.

The present antibodies can be used to detect the presence of the present Bbk protein in a human tissue sample. The present Bbk protein can be detected by contacting the sample with an imaging-effective amount of the present detectably labeled appropriate antibody and detecting the label, thereby establishing the presence of the Bbk protein in the sample. Detection can be carried out by imaging in vivo. The Bbk protein can also be detected by known immunoassay techniques, including, for example, RIA, ELISA, etc., using appropriate antibodies according to the invention.

The antibodies of the present invention are prepared by any of a variety of known methods. For example, cells expressing the Bbk protein can be administered to an animal in order to induce the production of serum containing polyclonal antibodies that are capable of binding the Bbk protein. For example, the Bbk protein or fragment thereof is chemically synthesized and puritfed by HPLC to render it substantially tree of contaminants. Such a preparation is then introduced into an animal in order to produce polyclonal antisera of high specific activity.

Polyclonal antibodies can be generated in any suitable animal including, for example, mice, rabbits or goats. The Bbk immunogenic peptide or fragment thereof can be injected by itself or linked to appropriate immunoactivating carriers, such as Keyhole limpet hemocyanin (KLH). See Catty, D., Ed.,*Antibodies, A Practical Handbook*, Vols. I and II, IRL Press, Washington, D.C. (1988).

Monoclonal antibodies can be prepared in various ways using techniques well understood by those having ordinary skill in the art. For example, monoclonal antibodies can be prepared using hybridoma technology (Kohler, et al., *Nature* 256:495 (1975); Kohler, et al.,*Eur. J. imninol*. 6:511 (1976); Kohler, et al., *Eur. J. Immunol*. 6:292 (1976); Hammerling, et al., In: *Monoclonal Antibodies and T-Cell Hybridomas*, Elsevier, N.Y., pp. 563–681 (1981)); Roger H. Kennett, et al., Eds., *Monoclonal Antibodies - Hybridomas: A New Dimension in Biological Analysis*, Plenum Press (1980). In general, such procedures involve immunizing an animal with the present Bbk protein, or a fragment thereof. The splenocytes of such animals are extracted and fused with a suitable mycloma cell line. Any suitable mycloma cell line may be employed in accordance with the present invention. After fusion, the resulting hybridoma cells are selectively maintained in HAT medium, and then cloned by limiting dilution as described by Wands, et al., *Gastroenterol*. 80:225–232 (1981). The hybridoma cells obtained through such a selection are then assayed to identify clones which secrete antibodies capable of binding the Bbk protein.

Through application of the above-described methods, additional cell lines capable of producing antibodies which recognize epitopes of the present Bbk protein can be obtained.

For example, additional hybridomas which produce monoclonal antibodies which enable the detection of the present Bbk protein can be easily produced and isolated with minimal screening. Hybridomas producing monoclonal antibodies specific for epitopes which are found on the present Bbk protein are most effectively produced by first immunizing an animal from which hybridomas can be produced such as, for example, a Balb/c mouse, with initial subcutaneous injections of Freund's adjuvant, followed by booster injections within a few days. The fusion can be carried out using any of the techniques commonly known to those of ordinary skill in the art. The screening of the hybridomas to determine which ones are producing monoclonal antibodies specific for the present peptide is straightforward and can be accomplished in a standard ELISA or RIA format. For example, in an RIA screening forrnat the culture supernatant, or ascites fluid from a hybridoma producing monoclonal antibody is reacted with $^{125}$I-peptide. The isolation of other hybridomas secreting mAbs of the same specificity as those described herein can be accomplished by the technique of anti-idiotypic screening. Potocmjak, et al., *Science* 215:1637 (1982). Briefly, an anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb raised against the present Bbk protein or fragment thereof to which an anti-Id is being prepared. The immunized animal will recognize and respond to the idiotypic determinants of the immunizing antibody by producing an antibody to these idiotypic determinants (the anti-Id antibody).

By using an anti-Id antibody which is specific for idiotypic determinants on a given mAb, it is then possible to identify other B cell or hybridoma clones sharing that idiotype. Idiotypic identity between the antibody product of two clones makes it highly probable that the antibody products of the two clones recognize the same antigenic epitopes.

The anti-Id antibody may also be used as an "immunogen" to induce an immune response in yet another animal, producing a so-called anti-anti-Id antibody. The anti-anti-Id may be epitopically identical to the original mAb which induced the anti-Id.

Thus, by using antibodies to the idiotypic determinants of a mAb, it is possible to identity other clones expressing antibodies of identical specificity.

Accordingly, mAbs generated against the present Bbk protein may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for the antigen epitope. The anti-Id mAbs thus have their own idiotypic epitopes, or "idiotopes" structurally similar to the epitope being evaluated.

For replication, the hybridoma cells of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Of special interest to the present invention are antibodies which are produced in humans, or are "humanized" (i.e., non- immunogenic in a human) by recombinant or other technology such that they will not be antigenic in humans, or will be maintained in the circulating serum of a recipient for a longer period of time.

Humanized antibodies may be produced, for example by replacing an immunogenic portion of an antibody with a corresponding, but non- immunogenic portion (i.e., chimeric antibodies) (Robinson, et al., International Patent Publication PCT/US86/02269; Akira, et al., European Patent Application 184,187; Taniguchi, M., European Patent Application 171,496; Morrison, et a., European Patent Application 173, 494; Neuberger, et al., PCT Application WO 86/01533, Cabilly, et al., European Patent Application 125,023; Better, et al., *Science* 240:1041–1043 (1988); Liu, et al., *Proc. Natl. Acad. Sci. USA* 84:3439–3443 (1987); Liu, et al., *J. Immbunol.* 139:3521–3526 (1987); Sun, et al., *Proc. Natl. Acad. Sci. USA* 84:214–218 (1987); Nishimura, et al., *Canc. Res.* 47:999–1005 (1987); Wood, et al., *Nature* 314:446–449 (1985)); Shaw, et al., *J. Natl. Cancer Inst.* 80:1553–1559 (1988). General reviews of "humanized" chimeric antibodies are provided by Morrison, S. L. (*Science*, 229:1202–1207 (1985)) and by Oi, et al., *BioTechniques* 4:214 (1986)).

Suitable "humanized" antibodies can be alternatively produced as described by Jones, et al., *Nature* 321:552–525 (1986); Verhocyan, et al., *Science* 234:1534 (1988), and Beidler, et al., *J. Immninol.* 141:4053–4060 (1988).

The present Bbk protein, fragments thereof, hybrids thereof, Bbk mutants, or antibodies thereto can be utilized in immunoassays for the detection of the Bbk protein in a human tissue sample. For example, antibodies against the present Bbk protein can be used to detect the present Bbk protein in a human tissue sample. The immunoassays can be competitive or sandwich, as is otherwise well known and they all depend on the formation of antibody-antigen immune complex. These assays are well known to those of skill in the art.

For purposes of the assays, the antibody or antigen can he immobilized or labeled. There are many carriers to which the antibody/antigen can be bound for immobilization and which can be used in the present invention. Well-known carriers include but are not limited to glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding the antibody or antigen, or will be able to ascertain such, using routine experimentation.

Depending on the particular embodiment of the invention, one or more of the antibodies or antigen(s) peptide(s) will be coupled with a detectable label such as an enzyme, radioactive isotope, fluorescent compound, chemiluminescent compound, or bioluminescent compound.

Those of ordinary skill in the art will know of other suitable labels for binding to the antibodies or antigen(s) peptide(s) or will be able to ascertain such using routine experimentation. Furthermnore, the binding of these labels to the antibodies or antigen(s) can be done using standard techniques commonly known to those of ordinary skill in the art.

The antibodies or antigen peptide(s) can be bound to an enzyme. This enzyme, in turn, when later exposed to its substrate will react with the substrate in such a manner as to produce a chemical moiety which can be detected, as, for example, by spectrophotometric or fluorometric means. Examples of enzymes that can be used to detectably label are amylate dehydrogenase, staphylococcal nuclease, delta-5-steroidisomerase, yeast alcoholdehydrogenase, α-glycerophosphate dehydrogenase, triose phosphate isomerase, alkaline phosphatase, asparaginase, glucose oxidase, β-galactosidase, ribonuclease, urease, catalase, glucose-6-phosphate dehydrogenase, glucoamylase, and acetylcholinesterase.

The presence of an antibody or antigen can also be detected by labeling the antibody or antigen with a radioactive isotope. The presence of the radioactive isotope can be determined by such means as the use of agamma counter or a scintillation counter. Isotopes which are particularly useful are $^3$H, $^{125}$I, $^{32}$P, $^{35}$S, $^{14}$C, $^{51}$Cr, $^{36}$Cl, $^{57}$Co, $^{59}$Fe, $^{75}$Se, and $^{152}$Eu.

It is possible to detect the presence of the antibody or antigen by labeling the antibody or antigen peptide with a fluorescent compound. When the fluorescently labeled antibody or antigen peptide is exposed to light of the proper wavelength, its presence can then be detected due to fluorescence of the dye. Among the most common fluorescent labeling compounds are fluorescein isothiocyanate, rhodamine, phycoerythrin, phycocyanin, allophycocyanin, o-phthaldehyde, and fluorescamine.

Another way in which the antibody or antigen can be detectably labeled is by coupling it to a chemiluminescent compound. The presence of the chemiluminescent-tagged antibody or antigen peptide is then determined by detecting the presence of luminescence that arises during the course of a chemical reaction. Examples of particularly useful chemiluminescent labeling compounds are luminol, isoluminol, aromatic-acridinium ester, imidaxole, acridinium salt, and oxalate ester.

Likewise, a bioluminescent compound may also be used to label the antibody or antigen peptide. Bioluminescence is a special type of chemiluminescence which is found in biological systems and in which a catalytic protein increases the efficiency of the chemiluminescent reaction. The presence of a bioluminescent binding partner would be determined by detecting the presence of luminescence. Important bioluminescent compounds for purposes of labeling are luciferin, luciferase, and aequorin.

The antibodies or antigen peptide(s) for use in the assay of the invention are ideally suited for the preparation of a kit. Such a kit may comprise a carrier means being compartmentalized to receive in close confinement one or more container means such as vials, tubes, and the like, each of said container means comprising one of the separate elements to be used in the method.

For example, one of the container means may comprise a first antibody bound to an insoluble or partly soluble carrier. A second container may comprise soluble, detectably-labeled second antibody, in lyophilized form or in solution. The carrier means may also contain a third container means comprising a detectably labeled third antibody in lyophilized form or in solution. Such a kit can be used for sandwich assays.

In addition, the carrier means may also contain a plurality of containers each of which comprises different, predetermined amounts of the present Bbk peptide. These latter containers can then be used to prepare a standard curve into which can be used to interpolate the resultsobtained from the sample containing the unknown amount of the present Bbk protein.

Imaging can be carried out in vitro or in vivo. In vitro imaging can be done with the labels mentioned previously. In vivo imaging is done with diagnostically effective labeled antibodies. The term "diagnostically effective" means that the amount of detectably labeled antibody administered is sufficient to enable detection of the site of Bbk protein presence when compared to a background signal.

Generally, the dosage of detectably-labeled antibody or antigen(s) for diagnosis will vary depending on considerations such as age, condition, sex, and extent of disease in the patient, counterindications, if any, and other variables, to be adjusted by the individual physician. Dosage can very from 0.01 mg/kg to 2,000 mg/kg, preferably 0.1 mg/kg to 1,000 mg/kg.

The term "diagnostically labeled" means that the antibody has attached to it a diagnostically detectable label.

There are many different imaging labels and methods of labeling known to those of ordinary skill in the art. Examples of the types of labels which can be used in the present invention include radioactive isotopes and paramagnetic isotopes.

For diagnostic in vivo imaging, the type of detection instrument available is a major factor in selecting a given radionuclide. The radionucleotide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionucleotide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140–200 ke V range, which may be readily detected by conventional gamma cameras.

For in vivo diagnosis, radionucleotides may be bound to antibody or antigen either directly or indirectly by using an intermediary functional group. Intermediary functional groups which are often used to bind radioisotopes which exist as metallic ions to antibody or antigen are diethylenetriaminepentaacetic acid (DTPA) and ethlenediaminetetracetic acid (EDTA). Typical examples of metallic ions which can be bound to immunoglobulin are $^{99m}Tc, ^{123}I, ^{111}In, ^{131}I, ^{97}Ru, ^{67}Cu, ^{67}Ga, ^{72}As, ^{89}Zr,$ and $^{201}Tl$.

The antibodies used in the method of the invention can also be labeled with paramagnetic isotopes for purposes of in vivo diagnosis. Elements which are particularly useful (as in magnetic resonance imaging (MRI) techniques) in this manner include $^{157}Gd, ^{55}Mn, ^{162}Dy, ^{52}Cr,$ and $^{56}Fe$.

Preparations of the imaging antibodies for administration include sterile aqueous or non-aqueous solutions, suspensions, and emulsions. Examples of non-aqueous solvents are propyleneglycol, polyethyleneglycol, vegetable oil such as olive oil and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, and inert gases and the like. See, generally, *Remington's Pharmaceutical Science*, 16th ed. Mac Eds. 1980.

Of course, the expressed Bbk protein is an intracellular protein. Accordingly, those of skill will recognize that in vivo diagnostic and therapeutic methods employing the antibodies of the invention may require some mechanism by which such antibodies can detect Bbk in the cell. One such method is to introduce the antibodies or fragments thereof into the cell itself across the cell membrane. This may be accomplished, for example, by attaching the antibody to a ligand for which the target cell contains receptor sites. The antibody can thus be transported into the cell membrane or across the cell membrane along with the ligand. Suitable ligands include growth factors and cytokines that are internalized upon receptor binding. Suitable growth factors include epidermal growth factor (EGF), tumor growth factor alpha (TGF-α), fibroblast growth factor (FGF), insulin, and insulin-like growth factors 1 and 2 (IGF- 1 and IGF-2). Suitable cytokines include G-CSF, GM-CSF, erythrol)oietin, IL-1 and IL-2. It is noted that there are also receptors that carry nutrients and vitamins into cells. These nutrients are suitable for use as ligands in the present invention and include folate, dihydrofolate, tetrahydrofolate and vitamin B12.

The choice of a carrier ligand will depend on several factors, as those of skill will appreciate. These include, for example, the kinetics of the ligand and its receptor, and of overall transport, which may include passive or active, with actively transported ligands preferred. The means of attaching the antibody to the ligand also will vary within limits, and may be, for example, covalent or ionic, bearing in mind that such attachment should not unacceptably alter ligand-receptor affinity.

Examples of receptors suitable for such applications include the receptor for low density lipoprotein (LDL), which has been shown to contain all the information necessary for receptor endocytosis, Davis et al., *J. Cell Biol.* 107(6/3): Abstr. No. 3112 (1988), as well as known brain-specific receptors such as those for dopamine. In this regard, it will be appreciated that the ligand may itself be an antibody or fragment specific for the receptor, to which may be conjugated the antibody of the invention.

Moreover, those of skill may find it particularly desirable to employ antibody fragments of the invention (such as, for example, Fab or F(ab')$_2$ fragments), which are less likely to interfere with the ligand-receptor interaction, and may be more easily transported across the cell membrane. Single-chain antibodies may prove preferable for these and other reasons, as will be appreciated by those of skill.

When an antibody is to be transported into the cell's membrane or into the cell as described above, it will be preferred to diagnostically or therapeutically label the antibody in such a way that the label will be relatively more effective when the antibody is bound to its antigenic site on the Bbk protein. This may be accomplished, for example, by employing a label which becomes active or detectable as a result of formation of the antigen-aintibody complex. Alternatively, the antibody itself may be labeled in such a way that antigen-antibody complex formation induces a conformational change in the antibody to expose or more fully expose the previously unexposed or less fully exposed label. All of the above criteria, and others, will be apparent to those of skill in carrying out these aspects of the invention.

It is also possible to utilize liposomes having the antibodies of the present invention in their membranes to specifically deliver the antibodies to the target area. These liposomes can be produced so that they contain, in addition to the antibody, such therapeutic agents as drugs, radioisotopes, lectins and toxins, which would act at the target site.

Pharmaceutical Compositions

Pharmaceutical compositions containing a therapeutically effective amount of the present Bbk protein, functional equivalents, fragments and/or hybrids an/or mutants thereof, as well as vectors containing cDNA encoding one or more of the foregoing, are useful for treating patients suffering from degenerative disorders characterized by inappropriate cell death or inappropriate cell proliferation.

Hybrids of Bbk include hybrids of Bbk and for example Bcl-2, ced-9, Bcl-X$_L$, Bcl-X$_S$, Bax, Mcl-1, c-myc, LMW5-HL, BHRF-1, Bak, Bik and A1. Such hybrids exhibit enhanced, decreased or intermediate apoptosis induction or suppression activity as compared to the activity of Bbk alone. These hybrids can be readily selected, produced and employed by one or ordinary skill in the art. Pharmaceutical compositions according to the invention thus will contain a therapeutically effective amount of the present Bbk protein, functional equivalents, fragments and/or hybrids and/or mutants thereof, and may optionally contain one or more pharmaceutically acceptable carriers and/or excipients, known to those of ordinary skill in the art. Administration, dosage and frequency, and length of the course of treatment can be readily optimized for a particular patient by one of ordinary skill in the art For example, the present pharmaceutical composition can be formulated as sterile aqueous or non-aqueous suspensions or emulsions, as described above, for example for solutions for intravenous administration.

Therapeutic Applications

Programmed cell death is a process in which cells undergo nuclear condensation and fragmentation during normal development of healthy tissues and organs. The process is essential in maintaining the balance between growth of new cells and elimination of old cells. When apoptosis does not work properly, either by causing cells to die prematurely or by preventing them from dying when scheduled, various disorders develop.

The present apoptosis associated Bbk protein, functional equivalents, fragments and/or hybrids and/or mutants thereof as well as vectors containing cDNA encoding the foregoing are useful for treating degenerative disorders, which disorders are characterized by inappropriate cell death or inappropriate cell proliferation. Particular disorders may involve different cell types whereby it may be desirable to induce apoptosis in one cell type while suppressing apoptosis in the other. For example, it may be desirable to suppress apoptosis in lung tissue cells in a patient suffering from acute lung injury by administering the Bbk mutant protein of the invention (or by effecting expression of such Bbk mutant protein in those cells) while inducing apoptosis in fibroblast cells which may be present in the lung due to the inflammatory response by administering the Bbk protein of the invention (or by effecting Bbk protein expression in those cells).

The therapeutic agents of the present invention can be administered as discussed above with the requirement that the agent must cross the cell membrane. The therapeutic agent can be administered alone, in combination with or during the course of treatment with other acceptable therapies known in the art for treating a particular disorder. For example, the present therapeutic agents can be administered to induce apoptosis in a cancer patient who is also undergoing classic cancer therapy including, for example, radiation therapy, chemotherapy, and treatment with anti-cancer drugs including, for example, topoisomerase inhibitors, alkylating agents, antimetabolites, and hormone antagonists. Further, the present therapeutic agents can also be administered concurrently with gene therapy. For example, the present therapeutic agents can be administered to a patient suffering from a degenerative disorder of the central nervous system while the patient is concurrently undergoing gene therapy to replenish neutrophic hormones.

Premature widespread apoptosis (inappropriate cell death) causes much of the damage associated with degenerative disorders including, for example, AIDs, chemotherapy and radiation, and tissue atrophy. In AIDs patients, lymphocytes are activated even in the asymptomatic phase of the HIV infection, and those cells die prematurely by apoptosis. Such disorders may admit of treatment by administration of a Bbk mutant protein.

Those of skill will appreciate that administration of the various proteins of the invention to particular target cells or tissues, as described herein, is intended to comprehend the administration of the proteins themselves as well as the expression by the target cells or tissues of the nucleotide sequences encoding those proteins by various known means and in accordance with the teachings of the present specification.

Degenerative disorders characterized in inappropriate cell proliferation include cancer, autoimmune disorders, tissue hypertrophy, and inflammatory disorders including inflammation arising from acute tissue injury including, for example, acute lung iniury. These disorders can be treated by administering the present Bbk protein or functional equivalent.

Cancers arise when changes in DNA cause the anomalous accumulation of cells. The comparative rates of cell division and cell deaths determine how fast a cancer grows. Some cancer cells divide more slowly than normal cells, but the cancer may still expand because of prolonged cell life span. Apoptosis is an efficient method for preventing malignant transformation because it removes cells with genetic lesions. Defective apoptosis can promote cancer development, both by allowing accumulation of dividing cells and by obstructing removal of genetic variants with enhanced malignant potential. The present therapeutic agents, including the present Bbk protein, functional equivalents, fragments, and hybrids thereof, along with vectors containing cDNA encoding the one or more of the foregoing, can be administered to cancer patients to induce apoptosis.

Many types of cancer can be treated by the administration of the present therapeutic agents, including for example, carcinomas, sarcomas, and leukemia/lymphomas, including for example, carcinomas such as adenocarcinomas, squamous carcinomas, carcinoma of the organs including breast, colon, head, neck, etc.; sarcomas including chondrosarcoma, melanosarcoma, etc.; and leukemia and lymphomas including acute lymphomatic leukemia, acute myelogenous leukemia, non- Hodgkin's lymphoma, Burkitt's lymphoma, B-cell lymphomas, T-cell lymphomas, etc. Other conditions amenable to treatment using the present therapeutic agent include fungal infections.

The present therapeutic agents can be used to treat autoimmune diseases. Random gene recombination and somatic hypermutation can potentially generate autoreactive T and B lymphocytes throughout life. Under normal conditions immature lymphocytes that bind autoantigens die by apoptosis. However, a defect in the deletion of these lymphocytes predisposes one to autoimmunity.

The present therapeutic agents can be administered to patients suffering from autoimmune disorders to induce apoptosis in autoreactive T lymphocytes, for example, in patients suffering systemic lupus erythematosus. Other autoimmune diseases amenable to treatment by suppressing or inducing apoptosis through the administration of the present therapeutic agents include, for example, rheumatoid arthritis, myasthenia gravis, Grave's disease, Hashimoto's thyroiditis, insulin-resistent diabetes, allergic rhinitis, asthma, functional autonomic abnormalities, juvenile insulin-dependent diabetes, Addison's disease, idiopathic hypoparathyroidism, spontaneous infertility, premature ovarian failure, pemphigus, Bullous pemphigoid, primary biliary cirrhosis, autoimmune hemolytic anemia, idiopathic thrombocytopenic purpura, idiopathic neutropenia, Goodpasture's syndrome, rheumatoid arthritis and Sjogren's syndrome.

The present therapeutic agents can be used to treat inflammation resulting from acute lung injury, by inducing apoptosis. The disease process begins with an explosive inflammatory response in the alveolar wall. In the aftermath of the resulting tissue destruction, extensive fibroproliferation of the alveolar air space ensues, consisting of fibroblasts, capillaries and their connective tissue products. Fukuda, Y., et al., *Am. J. Pathol.* 126:171–182 (1987). An important mechanism for the systematic elimination of the foregoing is apoptosis, i.e., programed cell death.

The present therapeutic agents can also be used to treat degenerative disorders due to premature or excessive cell loss during aging which can lead to organ disfunction and disease. Such degenerative disorders include degenerative diseases of the central nervous system due to aging or other tactors which result in the death of neurons. The present therapeutic agents containing Bbk mutant protein or hybrids thereof can be administered to a patient suffering from such a degenerative disorder to suppress apoptosis. Further, the present therapeutic agents can be administered concurrently with gene therapy to provide genes encoding neutrophic hormones including, for example, nerve growth factor. Other conditions amenable to treatment utilizing the present therapeutic agents include, for example, Alzhcimer's disease.

One of ordinary skill in the art can readily identify other degenerative disorders characterized by inappropriate cell death or inappropriate cell proliferation or both which are amenable to treatment using the present therapeutic agents. The present therapeutic agents can include the Bbk protein itself, as well as fragments, functional equivalents and/or hybrids and/or mutants thereof, which are administered to a target cell. Alternatively, therapeutic agents according to the invention can be administered by infecting the target cell with a vector containing cDNA encoding one or more of the foregoing. The present therapeutic agents can be administered to the desired target cell as discussed below, for example, by choosing a receptor on the target cell surface which is specific for that cell type. The present therapeutic agents can be administered alone or in combination with other acceptable drug therapies. Further, the present therapeutic agents can be administered concurrently with other acceptable therapies specific for the particular degenerative disorder being treated. For example, the present therapeutic agents can be administered concurrently with chiemotherapeutic agents, gene therapy, or the like. Whether it is the Bbk protein itself or the a vector encoding the protein, the therapeutic agent must cross the cell membrane.

One method for introducing the Bbk protein or fragments thereof into the cell's membrane or into the cell itself is by attaching the protein to a ligand for which the target cell contains receptor sites. The protein can thus be transported into the cell membrane or across the cell membrane along with the ligand.

The choice of a carrier ligand will depend on several factors, as discussed herein and known to those of skill. Suitable tissue- specific receptors include: Brain: nerve growth factor receptor (NGF-R); breast: prolactin receptor; stomach: gastrin receptor; skin: melanocyte stimulating hormone receptor (MSH-R), liver: asialoglycoprotein receptor; thyroid: thyroid stimulating hon-one receptor (TSH-R); ovaries: luteinizing hormonereceptor (LH-R), testis: human chorionic gonadotrophin receptor (hCG-R), T-cells: T-cell receptors; B cells: CD19; lung hyaluronate receptor CD44 isoform 4V (J. Cell. Biol. 124, 7182, 1994). In this regard, it will be appreciated that the ligand may be an antibody or fragment specific for the receptor, to which may be conjugated the Bbk protein of the invention.

It may be desirable to employ active Bbk fragments according to the invention which are less likely to interfere with the ligand- receptor interaction, and which may be more easily transported across the cell membrane.

When a protein is to be transported across the cell's membrane or into the cell as described above and the ligand is an antibody, it will be preferred to diagnostically or therapeutically label the protein in such a way that the label will be relatively more effective when the protein is bound, such as, for example, by means analogous to those described herein in the context of antibody transport.

It is also possible to utilize liposomes having the proteins of the present invention in their membrane to specifically deliver the present Bbk proteins to the target area. These liposomes can be produced so that they contain, in addition to the Bbk protein, such other therapeutic agents including drugs, radioisotopes, lectins and toxins, which would be released at the target site.

A preferred manner for administering the Bbk encoding nucleotide sequences (and their functional equivalents and/ or hybrids and/or mutants) for diagnostic or therapeutic purposes is by the use of viral vectors. Suitable viral vectors for gene transfer include retroviruses (reviewed in Miller, et al., *Methods Enzyrmol.* 217:581–599 (1993)) including human immunodeficiency virus (HIV), adenovirus derivatives (for exanmples see Erzurum, et al., *Nucleic Acids Res.* 21:1607–12 (1993); Zabner, et al., *Nat. Genet.* 6:75–83 (1994); Davidson, et al., *Nat. Genet.* 3:219–223 (1993)), adeno-associated virus (AAV), (i.e., see Flotte, et al., *Proc. Natl. Acad. Sci. USA* 90:10613–7 (1993)) and Herpes virus sectors (i.e., see Anderson, et al., *Cell. Mol Neurobiol.* 13:503–15 (1993)). Other suitable viruses can be readily selected and employed by those of ordinary skill in the art. Other methods for DNA delivery include liposome mediated gene transfer (Alton, et al., *Nat. Genet.* 5:135–42 (1993); Nabel, et al., *Proc. Natl. Acad. Sci. USA* 90:11307–11 (1993)).

The use of viral vectors for introduction of genes into mammalian cells is also reviewed, for example, in Varmus, *Science* 240(4858):1427 (1988); Eglitis et al., *BioTechniques* 6,7:608 (1988); Jaenisch, *Science* 240(4858):1468 (1988); and Bernstein et al., *Genet. Eng.* (N.Y) 7:235 (1985).

For the purposes of the present invention, it may be preferred to employ an attenuated viral or retroviral strain. Thus, for example, it is possible to use as vectors for the DNA sequences of the invention retroviruses having attenuated cytopathicity, such as HIV- $2_{ST}$(Kong et al., *Science* 240(4858):1525 (1988)) or HIV-$2_{UC1}$ (Evans et al., *Science* 240(4858):1523 (1988)), which enter neural cells by a CD4-dependent mechanism (Funke et al., *J. Exp. Med.* 165:1230 (1987)). The neurobiology of HIV infections is described, for example, in Johnson et al., *FASEB J.* 2(14) :2970 (1988). Those of skill will be able to target different cell populations having known susceptibilities to viruses by the exercise of routine skill. For example, CD4 is known to have a variant transcript in the human brain, with its highest content in forebrain (Maddon et al., *Cell* 47:333 (1986). Possible methods to target retroviral gene expression to specific cell types are reviewed by Boris-Lawrie and ft. Temin Curr. Opin. Genet. Dev. vol. 3, p.102–9 (1993).

Ideally, then, the choice of a gene delivery system will be made by those of skill, keeping in mind the objectives of efficient and stable gene transfer, with an appropriate level of gene expression, in a tissue-appropriate manner, and without any adverse effects. See, for example, Wolff et al., *Rheum. Dis. Clin. North Am.* 14(2):459 (1988). With respect to delivery to a central nervous system target, many viral vectors, including HIV, offer the advantage of being able to cross the blood-brain barrier (Johnson et al., *FASEB J.* 2(14):2970 (1988)).

Diagnostic Applications

Antibodies raised against the present Bbk protein, fragments, functional equivalents, or hybrids or mutants thereof can be used to detect the Bbk protein in a human tissue sample, as well as to diagnose degenerative disorders associated with the expression of the Bbk protein. Further, such antibodies can also be used to monitor the progress of degenerative disorders associated with the expression of the Bbk protein.

Any source of human cells is suitable for use in the diagnostic testing in the present invention. The cells can be isolated from any human tissue including for example, heart, lung, tumor cells, brain, placenta, liver, skeletal muscle, kidney and pancreas. Extraction ot proteins from the cell sample may be performed by any of the many means known in the art. For example, cells may be lysed by a detergent by mechanical means. if desired, nucleic acids can be removed from the cell preparation by enzymatic digestion or by precipitation. Such means are well known in the art.

Antibodies can be generated which are immunoreactive with the Bbk proteins by the methods set forth herein. Appropriate antibodies can then be screened using the natural gene products of bbk.

The extracted proteins from the cell sample may be contacted with the antibody under suitable conditions for antibody-antigen complex formation. Generally, such conditions are physiological conditions. The protein extract may be bound to a solid support such a nitrocellular filter or a microtiter plate.

The antibody will generally hear a label which is a radio label, a florescent label, or an enzyme conjugate which under appropriate conditions produces, for example, a colored reaction product. Antibodies and antibody labeling are described herein and known to those of skill. Alternatively, if the antibody is not labeled, it can be detected by means of a second antibody from another species which is reacted with the first antibody. Suitable assay techniques, labels and means of detection are discussed herein.

A parallel sample to the test sample is employed to provide the control. The control sample consists of an equivalent amount of proteins extracted from cells, preferably in the same manner as those of the test sample. The amount of protein can readily be determined by employing techniques well known in the art, including, for exaniple, the Lowry or Bradford techniques. The cells used for preparing the control sample may be selected from cells of the same cell type as the test cells, isolated from a normal human not suffering from the degenerative disorder from which the human from which the test sample was taken suffers, cells of the same cell type as the test sample isolated from an established normal cell line, and cells from the human who is being tested, which cell type is different from the cell type of the test cells.

Test samples can also be screened for elevated levels of mRNA transcribed from the bbk gene, according to methods well known in the art. For example, RNA extracted from B-cells may be used, or alternatively mRNA may be isolated from total cellular RNA. The mRNA may be purified, for example, by affinity chromatography on oligo (dT cellulose) which binds to the poly (A) tract at the 3' end of most mRNA. As is well known to those skilled in the art, it is essential that ribonuclease activity be minimized during preparation and assaying.

A DNA probe may be selected from any of the protein coding sequences of the bbk gene. Preferably, the probe will be selected from sequences of the 5' or 1st exon of the gene so that RNA can be detected. Preferably, the probe contains at least 15 nucleotides of the bbk sequence. In order to perform the hybridization, it is desirable that the probe be single stranded. Thus, if the probe is double stranded, it should be denatured to a single stranded form. Means for denaturing are well known in the art, including alkali or heat treatment. The probe can then be contacted with the RNA derived from the cell sample under conditions where homologous RNA-DNA hybrids form and are stable. Such conditions are well known in the art. Means for detecting hybrids are many and well known, but often involve the use of radiolabeled probes and nucleases which degrade single stranded DNA. Other methods known in the art may be used.

Control samples can be derived from any of these cell sources described above for use in the antibody diagnostic tests. Samples and controls should preferably be prepared in parallel under similar conditions.

The diagnostic methods and compositions of the present invention are useful for determining whether a disease/degenerative disorder is linked to abnormal Bbk expression, to the expression of Bbk mutants, as well as for determining the effect of over expression or loss of expression of Bbk in animal models such as transgenic mice and/or homozygous null mice. Methods for determining whether a disease/degenerative disorder is linked to abnormal Bbk expression include analyzing Bbk expression in diseased tissue as compared to normal tissue by for example, Northern and/or Western blots, as well as by other assay methods readily chosen and employed by those of ordinary skill in the art. Once It has been determined that a disease/degenerative disorder is linked to abnormal Bbk expression, the disease/disorder can be diagnosed in an individual.

The following examples are offered by way of illustration, not by way of limitation.

EXAMPLES

A. Materials and Methods

1. Yeast two-hybrid analysis. Components of the yeast two-hybrid system were obtained from Clontech Laboratories (Catalog numbers K1605-1, K1605-D, HL4006AE). These included the GAL4 binding domain fusion vector pAS2, yeast strains Y190 and Y187, and human lymphocyte cDNA activation domain library. Bak was subcloned into the pAS2 vector using standard protocols (Sambrook, J., et al., *Molecular Cloning: A Laboratory Manual*, 2d Ed., Cold Spring Harbor Laboratory Press, Planview, N.Y. (1989)). To create an in-frame fusion with Bak the pAS2 vector was modified by digesting with NdeI, making the ends blunt with Klenow fragment of DNA polymerasc I, and re-ligating. The Bak gene was removed from pcDNA1/amp (described in co-pending U.S. application Ser. No. 08/321,071, filed 11 Oct. 1994, which is a continuation-in-part of U.S. application Ser. No. 08/287,427, filed 9 Aug. 1994 (bak is referred to therein as bcl-y)) by digestion with BamHI and EcoRI, made blunt with the Klenow fragment of DNA polymerase I, and ligated into the modified pAS2 vector that had been digested with SmaI and treated with calf intestinal phosphatase to remove terminal phosphates. The Bak/GAL4 binding domain fusion vector (pAS2/BakΔC) was DNA sequenced across the fusion point to verify that the GAL4 reading frame had been preserved through the cloning junction and into the Bak open reading frame. Two-hybrid analysis, β-galactosidase filter assays, and detection of false positives were performed using the Bak/GAL4 binding domain bait and lymphocyte cDNA GAL4 activation domain library following the manufacturer's instructions. Plasmid DNAs from the positive clones were isolated and transformed into *E. coli* as described by the manufacturer. Bacterial clones were analyzed further by restriction enzyme analysis and DNA sequencing.

2. Additional Plasmid Constructs. All plasmid constructs were made using standard protocols (Samnbrook, J., et al., *Molecular Cloning: A Laboratory Manual*, 2d Ed., Cold Spring Harbor Laboratory Press, Planview, N.Y. (1989)). A modified foim of the mammalian expression plasmid pcDNA3 (Clontech) was created in which the influenza hemagglutanin (HA) epitope tag (MGYPYDVPDYASLS) (SEQ ID NO:29) had been inserted between the HindIII and XhoI sites of the polylinker cloning region to generate pcDNA3/HA. The Bbk gene obtained in the two-hybrid screen (pACT/Bbk) was removed from the GAL4 activation domain plasmid on an XhoI fragment and subcloned into the XhoI site of the pcDNA3/HA vector described above to create pcDNA3/HABbk. This results in an in-frame fusion ol Bbk with the HA tag with the HA tag at the N-terminus of Bbk.

The deletion mutant Δ1–105 was obtained directly from the two-hybrid screen and subcloned in a manner simlar to full length Bbk to create pcDNA3/HAΔ1–105. The mutant pcDNA3/HAΔ142–249 was created by digesting pcDNA3/HABbk with PflMI and XbaI to remove sequences between nucleotides 338–958 and subsequently replacing the deleted sequences with a polymerase chain reaction (PCR) generated PflMI to XbaI DNA fragment corresponding to Bbk nucleotides 338–476. An in-frame stop codon was incorporated after amino acid 141.

The alanine point mutants pcDNA/HAPM-LVLEE ($L_{125}V_{129}L_{132}E_{134}E_{135}$ replaced with A residues), pcDNA/HAPM-V ($V_{129}$, replaced with A residue), pcDNA/HAPM-L ($L_{,132}$ replaced with A residue), pcDNA/HAPM-EE ($E_{134}E_{135}$ replaced with A residues) were created by replacing wild type Bbk sequences between nucleotides 338–476 (a PflMI fragment) with PCR-generated PflMI fragments that have incorporated alanine codons at the designated positions. Bbk genes carrying the alanine point mutations were removed from the pcDNA/HA vectors and also cloned into the XhoI polylinker site of pACT to create pACT/PM-LVLEE, pACT/PM-V, pACT/PM-L, and pACT/PM-EE. These plasmids generate an in-frame fusion between the Bbk mutants and the Gal4 activation domain for use in yeast two-hybrid analysis.

Plasmid pRcCMV/HABbkBH3 expressing Bbk amino acid residues 117–166, which encompass the Bbk BH3 domain, was constructed as described below. A fragment of the Bbk gene encoding amino acid residues 117–166 was generated by PCR (incorporating a stop codon after amino acid 166) and subsequently cloned into the XhoI site of pcDNA3/HA (see above) that had been made blunt with the Klenow fragment of DNA polymerase. The HA tag/Bbk BH3 fusion gene was then removed on an HindIII/XbaI fragment and subcloned into the HindII/XbaI sites of pRc-CMV (Clontech). This cloning results in the in-frame fusion of the HA tag and the Bbk BH3 domain for use in mammalian cell transfections. A control plasmid encoding wild type Bbk was similarly constructed by removing the HindIII/XbaI fragment from pcDNA3/HABbk (see above) and subcloning into the HindII/XbaI sites of pRcCMV.

A glutathione S-transferase fusion of Bbk (GST-Bbk) was created by subcloning a BglII to EcoRi fragment of Bbk into the BamHI to EcoRI sites of the plasmid pGEX2TK (Pharmacia). The BglII to EcoRI fragment of Bbk was created in several steps. First the initiating methionine of Bbk was removed by replacing a BglII to Bsu36I fragment of pcDNA3/HABbk with a double-stranded oligonuleotide adapter. The XbaI site of this modified pcDNA3/HABbk plasmid was then converted to an EcoRI site using EcoRI linkers.

Other plasmids expressing Bak, Bik, Bax, Bcl-$x_L$, Bcl-2 and Epstein Barr virus BHRF1 have been previously described (Boyd , J. M., et al., *Oncogene* 11:1921 (1995); Chittenden ,T. *EMBO J.* 14(22):5589 (1995); co-pending U.S. application Ser. No. 08/321,071, filed 11 Oct., 1994, which is a continuation-in-part of U.S. application Ser. No. 08/287,427, filed 9 Aug., 1994 (bak is referred to therein as bcl-y)).

3. Northern Blot Analysis. Human fetal and adult multiple tissue Northern blots were purchased from Clontech Laboratories and hybridized sequentially to $^{32}$P-labeled probes encompassing the entire coding regions of Bbk and β-actin following the supplier's protocol.

4. In vitro translation. $^{35}$S-methionine labeled proteins were synthesized in vitro using the TnT T7/T3 coupled reticulocyte lysate system (Promega), following the manufacturer's procedures. Translation products were subjected to SDS polyacrylamide electrophoresis. The gel was fixed, incubated in a flourography enhancing solution (Amplify, Amersham), dried, and subjected to autoradiography at −70° C.

5. Western blot analysis. COS7 cells were cultured in DMEM supplemented with 10%, fetal calf serum and L-glutamine. Cells were transfected with 2 μg of plasmid DNA using LipofectAMINE (Gibco/BRL), and cell lysates were prepared 24 hours after transfection. Portions of the cells' extracts (approximately 100 mg) were electrophoresed on an SDS polyacrylamide gel, and transferred to a nylon membrane by standard methods (Harlow, E., et al., *Antibodies: A Laboratory Manual* (1988)). The blot was incubated with the anti-HA epitope monoclonal antibody 12CA5 (Klodziej, P. A., et al., *Meth. Enzymol.* 194:508–519 (1991)), which was subsequently detected with a secondary antibody using the ECL system (Amersham).

6. Transient transfection analysis. Rat1, HeLa, and BT549 cells were cultured at 37° C., 7% $CO_2$ in DMEM with 10% fetal calf serum, 4 nM L-glutamine, 50 units/ml penicillin, and 50 μg/ml streptomycin. Cells were plated at $3.5=10^4$ cells/well in 24 well tissue culture dishes 24 hours before transfection. A plasmid encoding *E. coli* β-galctosidase (pRcCMV/βgal, 0.16 μg) was mixed with a total of 0.42 μg plasmid(s) of interest as defined in the figure legends. The plasmid mixture was added to 25 μl OPTIMEM (Gibco/BRL) and subsequently mixed with 27 μl LipofectAMINE solution (2 μl stock solution diluted with 25 μl OPTIMEM). After a 30 minute incubation at room temperature the plasmid mixtures were diluted with 200 μl OPTIMEM and added to cells that had been rinsed once with OPTIMEM. After 4 hours at normal growth conditions the cells were fed with 250 μl DMEM, 20% fetal calf serum, 4 mM L-glutamine and then allowed to grow for 24 hours under normal conditions. Cells were then washed with phosphate buffered saline (PBS), fixed with 2% gluteraldehyde, 2% parafoimaldehyde, 49.2 mM sodium phosphate (pH 7.3) for 5 minutes at 4° C. and washed twice with PBS. β-galactosidase-expressing cells are identified as blue cells after a 1–4 hour incubation with 80 mM $Na_2HPO_4$, 20 mM $NaH_2PO_4$, 1.3 mM $MgCl_2$, 1 mg/ml X-Gal (diluted from a 20 mg/ml stock solution prepared in dimethylformamide), 3 mM $K_3Fe(CN)_6$, 3 mM $K_4Fe(CN)_6/3H_2O$. Live blue cells are identified as those that retain a flat morphology while dead blue cells are round.

7. In vitro protein interactions. Glutathione S-transferase fusion protein of Bbk (GST-Bbk) was expressed in *E. coli* from plasmid pGEX2TK-Bbk and purified by affinity chromatography using glutathione agarose (Smith, D. B. and Johnson, K. S., *Gene* 67:31–40 (1988)). $^{35}$S-methionine labeled HA-epitope tagged Bak, Bax, Bik, and Flag-epitope (Kodak) tagged $Bcl-x_L$ was expressed iin vitro using a coupled transcription/translation system in rabbit reticulocyte lysates (Promega). Labeled proteins were precleared with 10% glutathione- agarose in 10 mM HEPES buffer (pH 7.2) containing 0.25% NP-40, 142.5 mM KCl, 5 mM $MgCl_2$, 1 mM EGTA (Buffer A). GST-Bbk was added (final concentration 1–3 μM) and the mixtures incubated for 60 minutes at 4° C. Protein complexes were captured with 10% glutathione-agarose and washed twice with buffer A and once with buffer A without NP-40. Proteins were eluted from the beads by incubation in SDS-PAGE sample bufler at 100° C. for 5 minutes and loaded onto 4–20% SDS-polyacrylamide gels (Novex). Following electrophoresis, gels were fixed and incubated in a flourotgraphy enhancing solution (Amplify, Amersham). The gels were dried and subjected to autoradiography at −70° C.

8. Liquid culture β-galactosidase assays. The affinity of Bbk/Bak and mutant Bbk/Bak interactions was quantitated using a liquid β-galactosidase assay with o-nitrophenylgalactoside (ONPG) as substrate as described by the manufacturer's protocol (Clontech). Plasmids used for analysis are as stated in the figure legends.

B. Results

1. Identification of Bak-interacting proteins by yeast two-hybrid analysis.

Bak is found expressed in many cells (co-pending U.S. application Ser. No. 08/321,071, filed 11 Oct., 1994, which is a continuation-in-part of U.S. application Ser. No. 08/287,427, filed 9 Aug., 1994, abandoned (bak is referred to therein as bcl-y); Kiefer, M. C., et al., *Nature* 374:736 (1995)). Overexpression of Bak induces death by apoptosis. It was believed that regulators or effectors of apoptosis might bind to Bak. Proteins that interact with Bak were therefore identified using the yeast two-hybrid system (U.S. Pat. No. 5,283,173). The principle of this methodology is summarized in FIG. 1.

GAL4 is a yeast transcriptional activator protein that has two distinct domains, the DNA-binding domain and the transcription activation domain (FIG. 1A). The DNA-binding domain binds to a specific DNA sequence element in the GAL4 promoter, thus bringing the transcription activation domain in proximity to the promoter where it functions to stimulate transcription. It has been demonstrated that these domains are separable, although when separated they cannot function to stimulate transcription. Transcriptional activation can, however, be restored if a link between the two separated domains is made. Such a link can be made by expressing the GAL4 domains as hybrid proteins where these domains are fused to heterologous proteins (protein X and protein Y in FIGS. 1B,C) that are known to interact. In the scenario shown in FIG. 1 the GAL4 binding domain serves to bring protein X to the GAL4 promoter and subsequent interaction with protein Y in turn brings the GAL4 activation domain to the promoter where it can stimulate transcription. The GAMA promoter, or a promoter containing the GAMA DNA sequence element, can be used to direct the transcription of selectable marker genes (such as HIS3) and reporter genes (such as lacZ).

The system described above can be used to study the interaction of proteins that are known to interact as well as to identify and isolate novel interacting proteins. In the latter case, a protein of interest is fused to the GAL4 binding domain and used as "bait" to capture interacting proteins that are expressed as GAL4 activation domain fusions. In the experiments described here a GAL4 DNA-binding domain/Bak fusion protein was used as the bait to isolate Bak-interacting proteins expressed as GAL4 activation domain fusions generated from a cDNA library of Epstein-Barr Virus-transformed human B lymphocytes (Clontech). Two-hybrid analysis, selection for interacting clones, β-galactosidase filter assays, and identification of false positives were performed following the manufacturer's specifications (Clontech).

2. Sequence analysis of an avid Bak-binding clone, bbk.

Eleven of the most avidly binding clones (as judged by the intensity of blue color in β-galactosidase filter assays) were determined by DNA sequencing to be varying length clones of the same gene. Restriction enzyme analysis was used to identify the approximate sizes of these clones. Clone bbk was the largest of the clones and was therefore chosen for exhaustive DNA sequencing of both the top and bottom strands. The sequence of clone bbk is shown in FIG. 2. Six of the eleven clones have the same sequence startpoint as bbk while there are five clones that have deletions of varying length (up to nucleotides 33. 151, 178, 242, and 364 of clone bbk). Three of the eleven clones have an intact 3' termintis as determined by the presence of a polyadenylated (polyA)

tail. The absence of a polyA tail in the remaining clones is likely to be due to abbenant priming during cDNA synthesis due to the AT-rich nature of the gene in this region. Nonetheless, the remaining clones have 3' termini that are within 30 bases of the true 3' terminus (including clone bbk, which is 10 bases short).

The sequence of bbk was compared to the Genbank database using the NCBI BLAST program. This analysis has identified numerous expressed sequence tag (EST) cDNAs (Accession Numbers: H26516, H42839, H59025, H59896, H59897, H72004, H72005, H89857, H90702, R02556, R02674, R07849, R07901, R36543, R38463, k58365, R78883, R78977, R85622) with significant homology (Poisson Sum P(N) values less than or equal to 5.5e–26) to bbk. These cDNAs also begin and end within several bases of the endpoint of bbk suggesting that bbk is a nearly full length clone.

Bbk encodes an open reading frame (ORF) of 249 amino acids beginning with nucleotide number 51 and ending at nucleotide number 799. This ORF is in the same frame as that predicted by the GAL4 activation domain which is fused N-terminal to Bbk. The sequence surrounding the predicted initiating methionine codon is consistent with the Kozak consensus sequence (Kozak, M. *Nucleic Acids Res.* 15:8125 (1987)) and there are no additional methionines or in-frame stop codons in the putative untranslated bbk sequence present between the Gal4 activation domain and the Bbk ORF. Thus, it is believed that the true ORF of the Bbk gene has been identified. It is interesting to note that several of the clones isolated by two-hybrid analysis, as well as several of the EST clones, have three additional nucleotides (AAG) not found in Bbk, between nucleotides 157 and 158 of Bbk. These nucleotides may be introduced as the result of alternate splice site usage. The addition of these three nucleotides in the putative coding region maintains the predicted reading frame and would serve to introduce an arginine residue at position 36. An analysis of protein databases using the putative Bbk ORF identified sequences of only limited homology. Thus, novel proteins that interact with the apoptosis-related protein, Bak, can be identified through the use of the two hybrid system.

3. Expression of Bbk mRNA in fetal and adult tissues.

Figure 3:
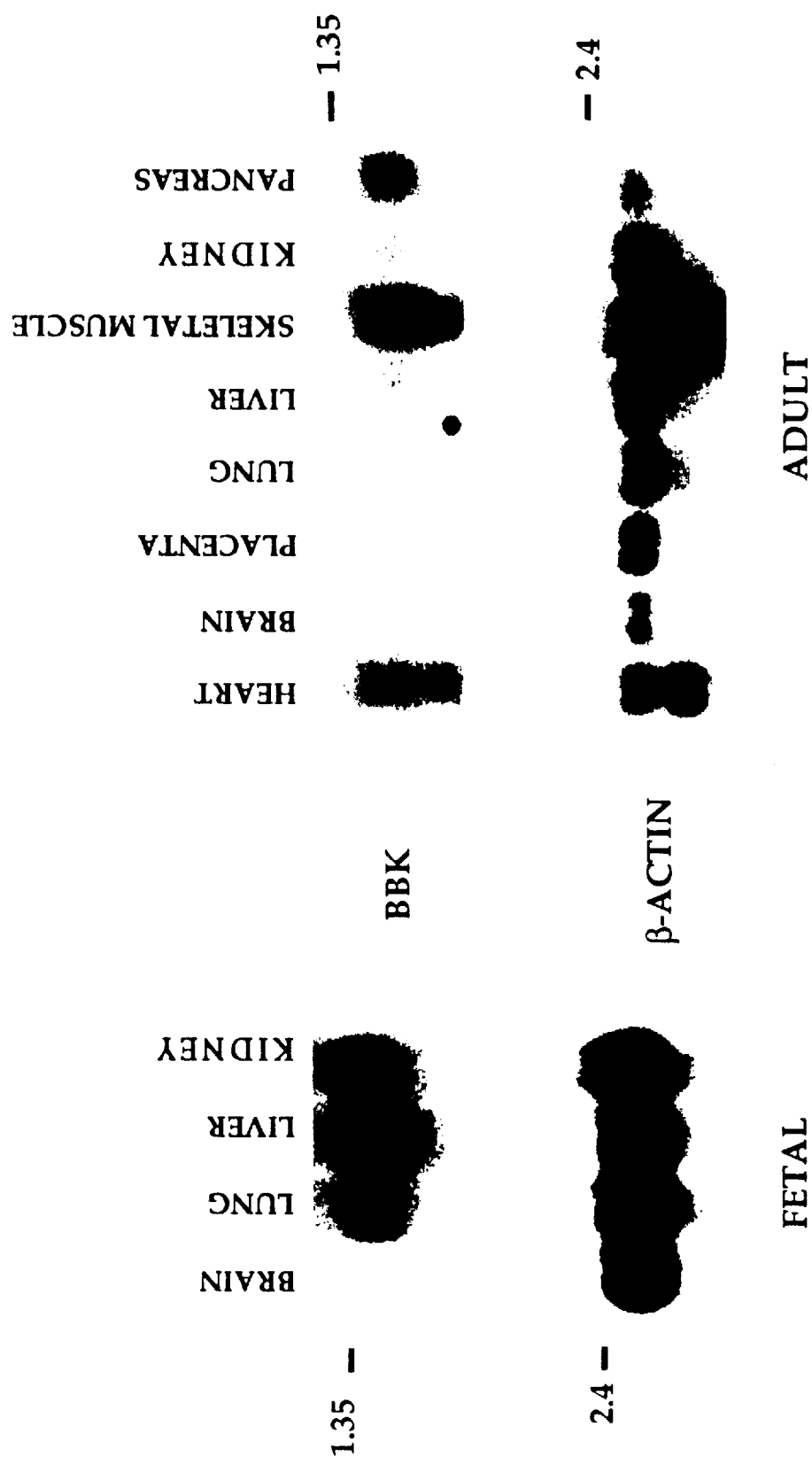
FIG. 3. Northern blot analysis of human fetal and adult tissues (Clontech). The blots were hybridized with $^{32}$P-labeled Bbk DNA (top panel) and β-actin DNA as a control. Size markers are as defined by the manufacturer.

Northern blot analysis was performed to determine the expression pattern and size of the Bbk messenger RNA. Northern blots of fetal and adult tissue probed with Bbk (FIG. 3) show that Bbk is a single mRNA species of approximately 0.8–1.2 kb. This message size is consistent with the notion that a full length clone has been isolated. The northern blot analysis also shows that Bbk is expressed in many diverse tissues with a distribution roughly similar to that of Bak (Kiefer, M. C., et al., *Nature* 374:736 (1995)) supporting the belief that Bbk and Bak may be complexed together in the cell.

4. Expression of Bbk in vitro and in transfected cells.

Figures 4A, 4B:
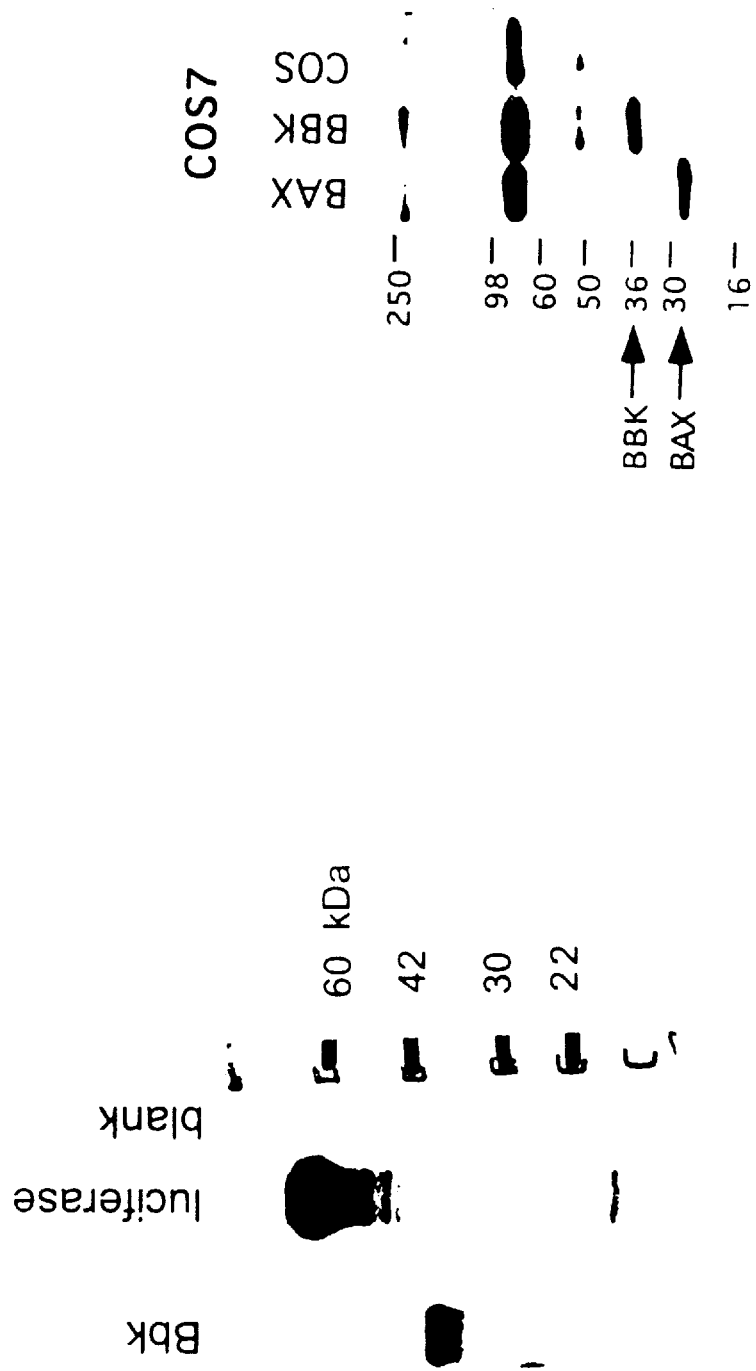
FIGS. 4A–4B. Expression of Bbk protein.

The deduced amino acid sequence of Bbk predicts a protein of MW 26.7 kD. The Bbk clone was subcloned from the yeast two-hybrid vector into pcDNA3 (Clontech) for in vitro expression using the T7 promoter and for mammalian expression using the human cytomegalovirus immediate early promoter. In order to detect the protein, the Bbk sequence was fused at the amino terminus to a 14 amino acid segment derived from the influenza hemaglutinin antigen (HA). This short peptide provides a well characterized epitope that permits immunological detection of the "tagged" protein by the monoclonal antibody 12CA5 (Boehringer Mannheim). In vitro transcription/translation of the Bbk clone in rabbit reticulocyte lysates produces a protein with electrophoretic mobility on SDS polyacrylamide gels corresponding to a molecular weight of about 37 kD (FIG. 4A), in approximate agreement with the size predicted from conceptual translation of the cDNA sequence plus the HA tag and nonspecific amino acids introduced by cloning. The pcDNA3 vector expressing HA-tagged Bbk was transfected into COS7 cells. Cell lysates were prepared 48 hours after transfection, and analyzed by Western blot with the anti-HA monoclonal antibody. The HA tagged Bbk protein, of the appropriate size, was detected in the COS7 cell extracts (FIG. 4B). These results demonstrate that the protein encoded by the isolated Bbk cDNA can be expressed both in vitro and in vivo.

5. Expression of Bbk accelerates cell death in Rat1, HeLa, and BT549 cells.

Figure 5A:
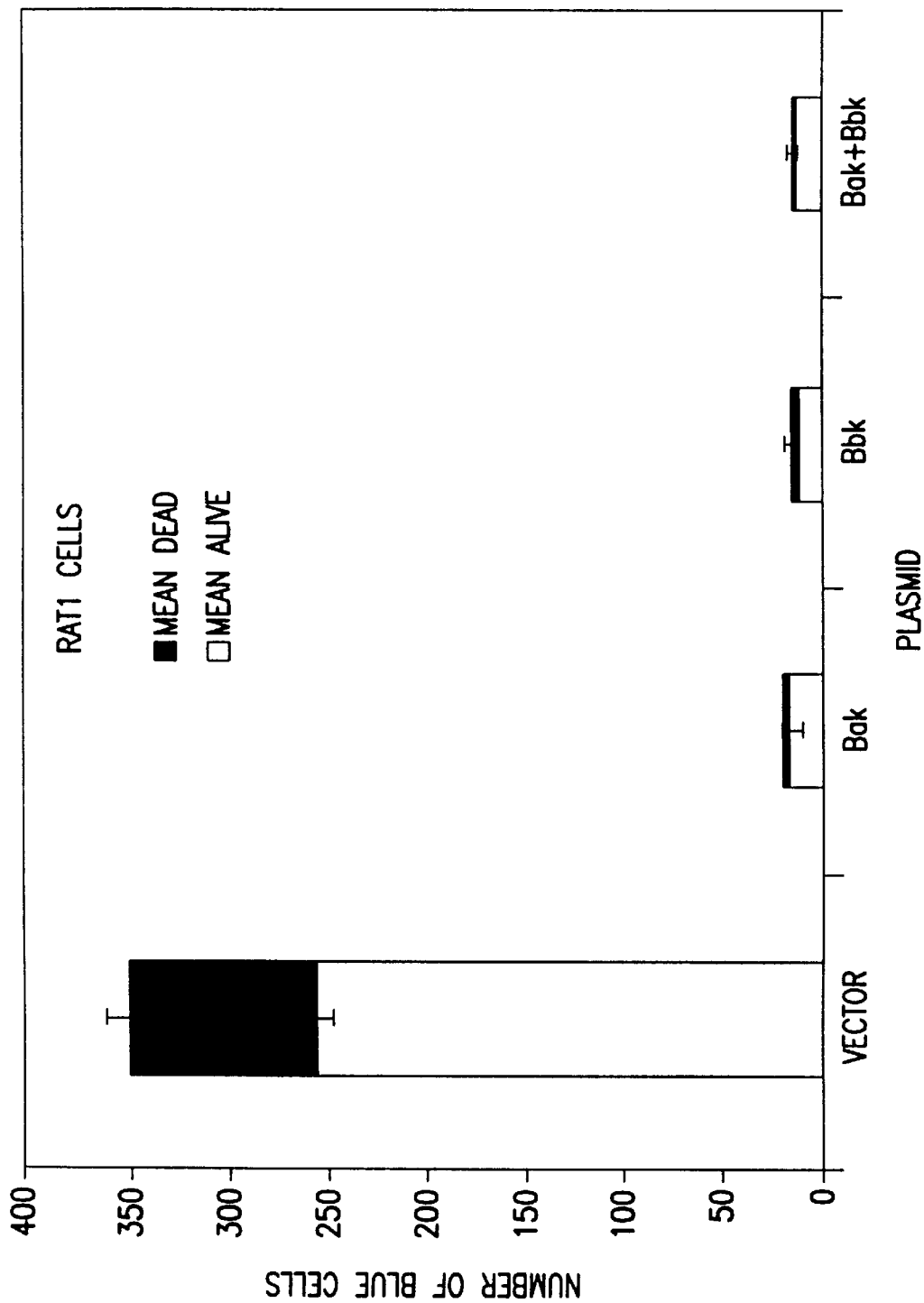
FIGS. 5A–5B. Effect of Bbk expression on viability of Rat1 cells. Cells were transfected with plasmids as indicated with a plasmid expressing β-galactosidase (pRcCMV/βgal, 0.16 μg). Cells were stained 24 hrs post-transfection to identify live and dead β-galactosidase expressing cells. Values from triplicate experiments were averaged and plotted with error bars representing SEM.

The HA-tagged Bbk clone expressed from the pcDNA3 vector was cotransfected with a plasmid expressing β-galactosidase into normal rat fibroblasts (Rat1 cells) and into human tumor lines HeLa and BT549, to determine the effect of Bbk expression on cellular viability. Such a cell death assay has been previously described (Miura, M., et al., *Cell* 75:653 (1993); Boyd, J. M., et al., *Oncogene* 11:1921 (1995); Chittenden, T., et al., *EMBO J.* 14(22):5589 (1995); co-pending U.S. application Ser. No. 08/440,391, filed 12 May, 1995; and consists of co-transfection of a gene of interest into cells with a β-galactosidase gene as a marker for transfectants. The effect of transfected gene products upon cellular viability is measured by scoring blue cells (β-galactosidase positive) relative to vector controls cells 24 hours post-translection. Inert or anti-apoptotic gene products are manifested as flat (live) blue cells in numbers similar to those of the vector controls, while detrimental gene products can be seen as an overall reduction in blue cell numbers or an increase in the frequency of round (dead) blue cells. The results in FIG. 5A clearly show a decrease in the number of blue cells when Rat1 cells are transfected with a plasmid expressing Bbk. Thus, it appears that, like its binding partner Bak, Bbk can induce cell death. Both Bak and Bbk can induce apoptosis when expressed individually in Rat1 cells. While not intending to be bound by a particular theory, this suggests either that the Bak/Bbk interaction is not necessary for the induction of apoptosis or that there are rat homologs of Bak and Bbk that can functionally interact with the human proteins. Alternatively, the interaction between these two proteins may serve a regulatory function to modulate their apoptotic potential. The data in FIG. 5A demonstrate that the co-expression of Bak and Bbk does not block the induction of apoptosis, suggesting that their ability to bind each other does not inhibit their ability to promote apoptosis. However, because Bak and Bbk each is a potent promoter of cell death individually, it was not possible in these assays to determine if their co-expression results in a cooperative induction of apoptosis.

Figure 5B:
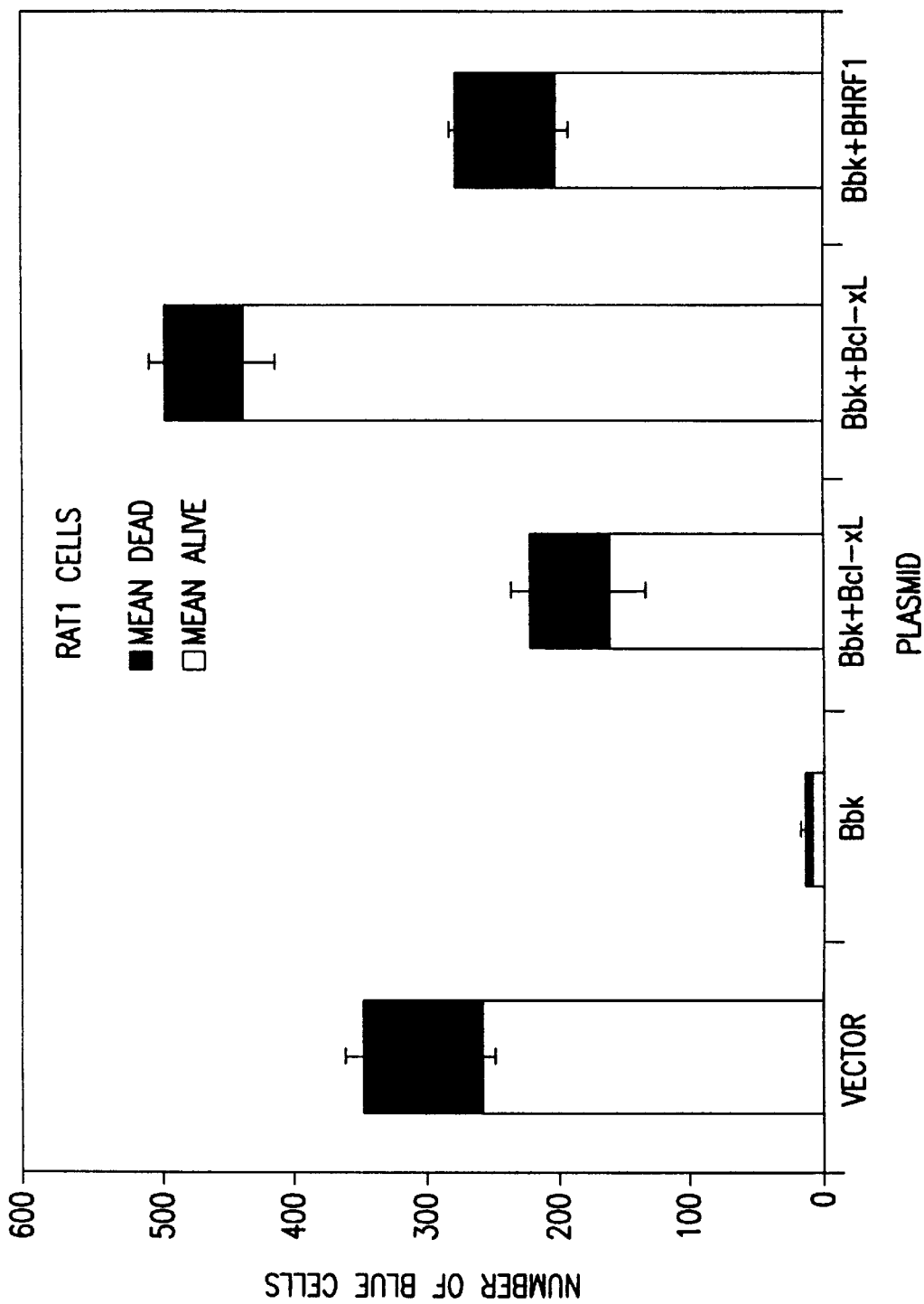

The apoptotic function of Bbk can be reversed by the coexpression of the known survival proteins, Bcl-2, Bcl-$x_L$, and Epstein-Barr virus BHRF1 (FIG. 5B). The extent of the cell death promoted by the apoptosis related proteins, Bak and Bik, is similarly reduced in the presence of the survival proteins (not shown). Increasing the ratio of the apoptosis-promoting protein, Bik, relative to these survival proteins can restore Bik cytotoxicity. This observation suggests that in the appropriate setting apoptosis promoting proteins can actually repress the action of survival proteins. The cell death promoting proteins may therefore be used to induce apoptosis in cells where survival is dependent upon the action of one of the Bcl-2 related cell survival proteins.

Figure 6A:
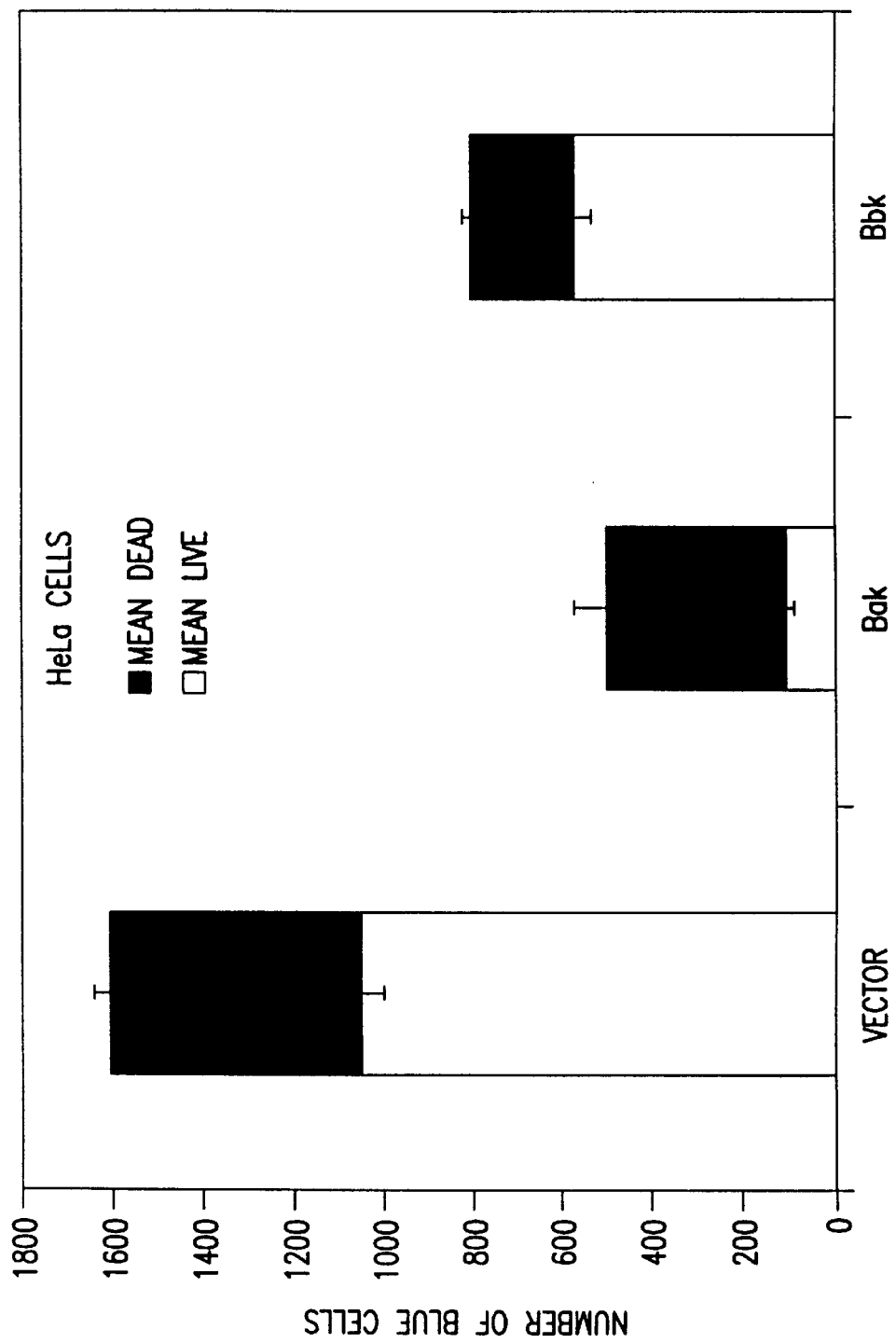
FIGS. 6A–6B. Effect of Bbk expression on viability of HeLa cells and BT549 cells.
Figure 6B:
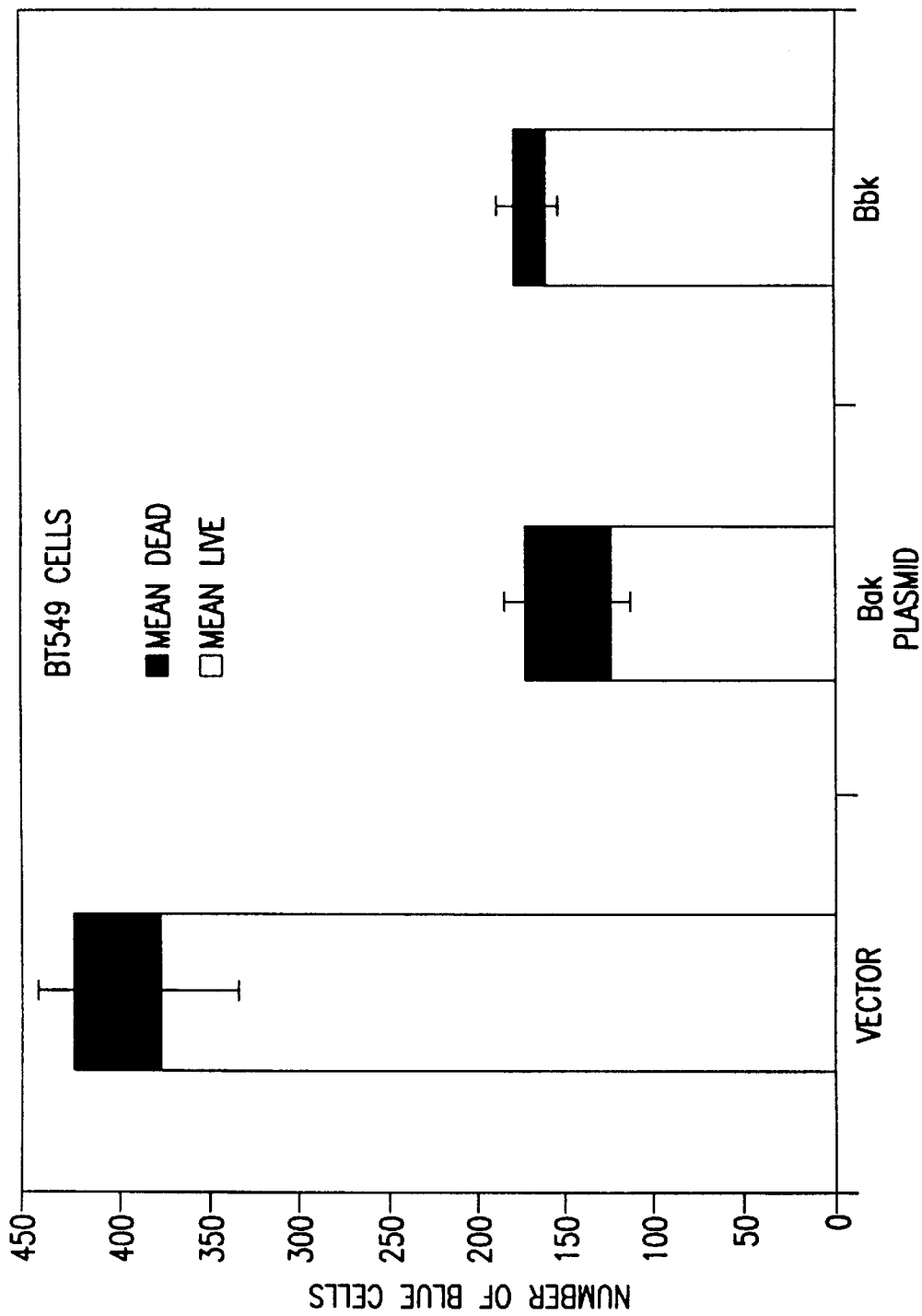

The ability of Bbk to induce apoptosis is also evident in the tumor cell lines, HeLa and BT549 (FIG. 6A, B). The extent of apoptosis induced by Bbk is comparable to that of Bak in the BT549 cells while in HeLa cells Bbk is somewhat less effective that Bak in the induction ot cell death. While Bbk can induce cell death, human tumor cells appear to display varying degrees of sensitivity to the apoptotic function of Bbk. Cells that are less sensitive to Bbk-induced apoptosis may, however, become more sensitive to conventional anti-cancer therapies subsequent to treatment with Bbk. Thus, a novel protein that binds Bak and induces apoptosis in a variety of cell types has now been identified.

6. Bbk interacts with Bak, Bax, Bcl-$x_L$ in vitro).

Figure 7:
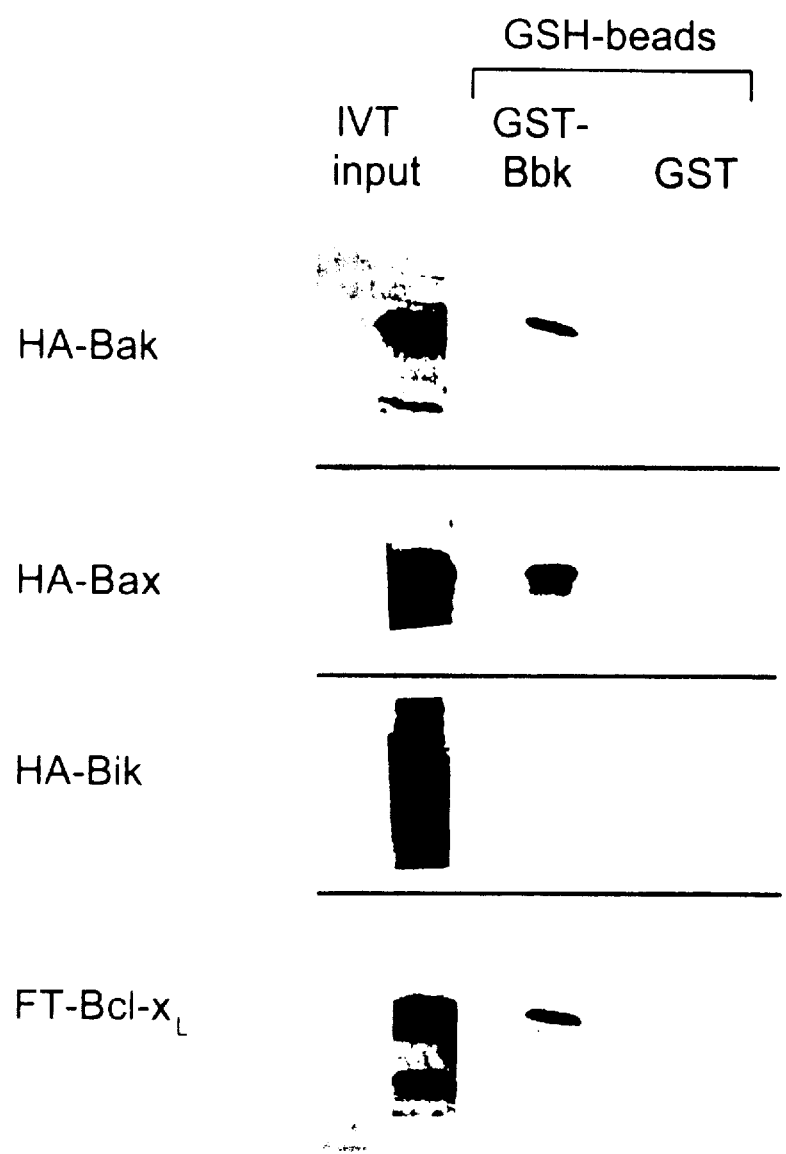
FIG. 7. Interaction of Bbk with Bcl-2 family members. A glutathione S-transferase (GST) fusion protein of Bbk was produced in *E. coli* and purified on glutathione agarose. Purified Bbk or GST control protein was incubated with $^{35}$S labeled in vitro translated (IVT) HA-tagged Bak, Bax, Bik or Flag-tagged Bcl-x$_L$. Complexes were captured on glutathione agarose beads, subjected to SDS gel elctrophoresis, and visualized by autoradiograhy. Captured complexes are compared to an aliquot of the input IVT material.

The reversal of Bbk induced apoptosis by cell survival members of the Bcl-2 family may suggest that these proteins can interact with Bbk. It was desired to determine if Bbk interacts solely with Bak or it it could also bind to other proteins known to be involved in apoptosis. A Glutathione S-transferase (GST)-Bbk fusion protein was expressed in *E. coli* and purified over glutathione-agarose. HA-tagged Bak, Bax, and Bik as well as Bcl-$x_L$ tagged with the FLAG epitope (Kodak) were radioactively labeled by in vitro translation and subsequently incubated with GST-Bbk or GST alone. Complexes were isolated on glutathione-agarose and analyzed by SDS-PAGE. FIG. 7 clearly shows Bbk interaction with Bak, BCl-$X_L$, and Bax but not with Bik. These interactons are specific, as the GST alone fails to complex with any of the in vitro translated material. Thus it appears that Bbk can interact with several members of the Bcl-2 family. Bbk does not appear to interact exclusively with the cell death inducing members of the Bcl-2 family, as demonstrated by it's interaction with Bcl-$X_L$, despite the fact that Bbk was isolated by virtue of its interaction with the cell death promoter, Bak. It is interesting to note that Bbk cannot, however, interact with Bik, a novel death inducing protein that shares the BH3 domain with Bcl-2 family members (Boyd, J. M., et al., *Oncogene* 11:1921 (1995)).

7. Bbk shares sequence homology with the Bcl-2 protein family.

The observations that Bbk interacts with several members of the Bcl-2 family and that it shares apoptosis related function suggested that Bbk might additionally share sequence homology. The database searches performed above did not reveal any sequence homology to Bcl-2 family members, however, a careful visual inspection identified a motif that is highly homologous to the BH2 domain of Bcl-2 and related family members (FIG. 8A). Alignment of the Bbk ORF with Bcl-2 family members using, the BH2 domain as an anchor did not reveal any homology to the BH1 domain of Bcl-2 but does show some homology (FIG. 8B) to the newly defined BH3 domain (co-pending U.S. application Ser. No. 08/440,391, filed 12 May, 1995, U.S. Pat. No. 5,656,725 (BH3 is referred to therein as the GD Domain)). Thus, Bbk appears to be a novel death-promoting member of the Bcl-2 protein family.

8. Bbk induced apoptosis is mediated by its BH3-like domain

It has been previously shown that the BH3 domain of Bak is both necessary and sufficient for its induction of cell death (co-pending U.S. application Ser. No. 08/440,391, filed 12 May, 1995, U.S. Pat. No. 5,656,725 (BH3 is referred to therein as the GD Domain)). Because Bbk shares a weak homology to the Bak BH3 domain, it was desired to determine whether this region provides a similar function for Bbk. To test this theory ai series of deletions that encroach upon the putative BH3 domain were made and tested in the Rat-1 cell death assay. The results in FIG. 9A show that two of these mutants, Δ1–105 (a deletion of the N-terminus to amino acid residue 106) and Δ142–249 (a deletion of the C-terminus beginning at amino acid residue 142), still retain the ability to induce apoptosis. These results suggest that a large portion of the Bbk molecule (including the BH2 domain) is dispensable for the cytotoxic activity of Bbk. Further, these data define the region between amino acids 106 to 141 as necessary for Bbk to induce cell death. Interestingly, this region coincides with the putative Bbk BH3 domain (residues 125–137). To definitively prove that this region was required for Bbk cytotoxicity, four alanine scanning mutants (FIG. 9B) that mutate several conserved residues were made and tested for their ability to induce apoptosis in Rat1 cells . The results shown in FIG. 9C demonstrate that PM-LVLEE, which contains five alamine substitutions in the BH3 element, has completely lost its apoptosis induction capabilities. To prove that the abolition of cytotoxicity in PM-LVLEE is not due to a failure to be synthesized, its expression was verified in COS7 cells where it was produced at levels comparable to those of wild type Bbk. The data therefore support the conclusion that the BH3 region of Bbk is absolutely necessary for its apoptotic function. The remaining mutants, PM-V, PM-L and PM-EE, are sin-le and double alanine mutations that were constructed to more precisely define the BH3 residues required for Bbk-induced apoptosis. The data in FIG. 9C demonstrate that each of these substitutions reduces, but does not abolish, the induction of cell death, indicating that all of the mutated residues are required in part for Bbk cytotoxicity. Again, each of these mutants was expressed in COS7 cells at levels comparable to those of wild type Bbk.

To determine if the Bbk BH3 domain was also sufficient to induce apoptosis, a plasmid expressing only amino acids 117–166 of Bbk (which includes the Bbk BH3 domain between residues 125–137) was transfected into Rat1 cells. The results in FIG. 10 show that expression of this 50 amino acid peptide encompassing the Bbk BH3 domain is sufficient to induce apoptosis. Thus, it appears that the BH3 domain of Bbk is analogous in function to the Bak BH3 domain, in that it is both necessary and sufficient for the induction of apoptosis.

9. Apoptosis induction by Bbk correlates with its ability to bind Bak.

Figure 11:
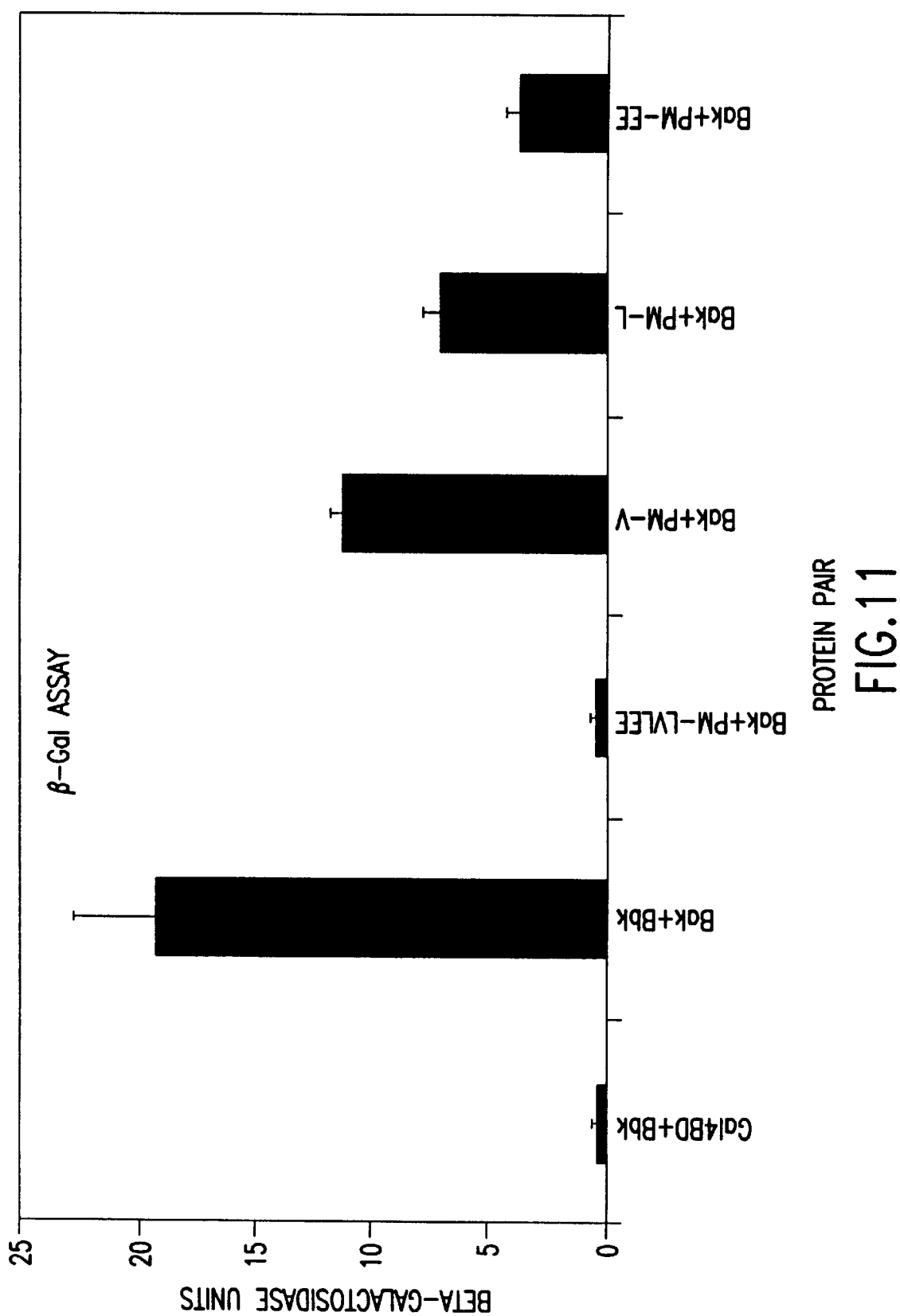
FIG. 11. Interaction of Bbk point mutants with Bak analyzed by yeast two-hybrid system. Bak bait plasmid (pAS2/BakΔC) was co-transformed into yeast with plasmids expressing Gal4 activation domain fusions of alanine point mutations of Bbk (pACF/PM-LVLEE, pACT/PM-V, pACT/PM-L, and pACT/PM-EE) and wild type Bbk (pACT/Bbk). As a positive control, plasmids supplied by the manufacturer (Clontech) expressing p-53 bait (pVA3) and SV40 T antigen (pTD1) were co-transformed as above. For a negative control, pACT/Bbk was co-transformed with pAS2, which expresses only the Gal4 activation domain as bait. Three individual colonies from each transformation were analyzed in triplicate for β-galactosidase activity using the liquid culture assay described by the manufacturer (Clontech). The mean of triplicate measurements from each of the three colonies were then averaged to generate a single value for each pair of interacting proteins. The data are plotted as units of β-galactosidase (Miller, J. H., *Experiments in Molecular Genetics*, Cold Spring Harbor Laboratory Press, Planview, N.Y. (1972)) with error bars representing the SEM.

Co-pending U.S. application Ser. No. 08/440.391, filed 12 May, 1995, U.S. Pat. No. 5,656,725 demonstrated that the Bak BH3 domain is responsible for its cytotoxic activity as well as its ability to bind the Bcl-$x_L$, an anti-apoptotic member of the Bcl-2 fanily. Since the Bbk BH3 domain appears to share the ability to induce apoptosis function in a manner similar to that of the Bak BH3 domain, it was of interest to determine whether the Bbk BH3 domain mediates the Bbk/Bak interaction. To test this possibility, the alanine mutations used above to define the apoptosis inducing domain of Bbk (PM-LVLEE, PM-V, PM-L, PM-EE) were fused to the Gal4 activation domain for use in the yeast two hybrid system with Bak as bait. In this assay, the expression levels of β-galactosidase are a measure of the affinity and/or stability of interaction between the two proteins, with high levels indicating a strong interaction and low levels indicating a weak interaction. FIG. 11 shows that PM-LVLEE, the Bbk mutant that has lost the ability to induce apoptosis, has also lost the ability to bind to Bak, as demonstrated by low levels of β-galactosidase (comparable to the negative control). The mutants that have retained intermediate levels of apoptotic potential (PM-V, PM-L, PM-EE) retain intermediate levels of interaction with Bak. This direct correlation between Bbk cytotoxicity and Bbk binding to Bak further supports the hypothesis that the Bbk/Bak interaction is required for the induction of apoptosis. Alternatively, there remains the possibility that there are additional binding partners for Bbk that also interact with its BH3 domain to effect cell death.

All publications mentioned in this specification are herein incorporated by reference, to the same extent as if each individual publication was specifically and individually indicated to be incorporated by reference. It will be understood that the invention is capable of further modifications and this application is intended to cover any variations, uses, or adoptions of the invention including such departures from the present disclosure as come within known or customary practice within the art to which the invention pertains, and is intended to be limited only by the appended claims.

---

What is claimed is:

1. An isolated Bbk protein comprising the amino acid sequence set forth as SEQ ID NO:11.

2. A composition comprising the Bbk protein of claim 1 and a carrier.

3. A method for inducing apoptosis in a nonapoptotic cell in vitro comprising expressing in said cell an amount of the Bbk protein of claim 1 effective to induce apoptosis in said cell.

4. An isolated peptide comprising the Bbk RH3 domain, wherein said domain comprises an amino acid sequence selected from the group consisting of the sequences set forth as SEQ ID NOS:5–8.

5. The peptide of claim 4 wherein said peptide consists of an amino acid sequence selected from the group consisting of:

LRRLVALLEEEAE (SEQ ID NO:5),
LRRLAALLEEEAE (SEQ ID NO:6),
LRRLVALAEEEAE (SEQ ID NO:7), and
LRRLVALLEAAAE (SEQ ID NO:8).

* * * * *

UNITED STATES PATENT AND TRADEMARK OFFICE
CERTIFICATE OF CORRECTION

PATENT NO    :    5,834,234

DATED        :    10 November 1998

INVENTOR(S)  :    GALLO, Gregory J.

It is certified that error appears in the above-identified patent and that said Letters Patent are hereby corrected as shown below:

In figure 8b, on the last line, "BCLX" should be - - BCL-X - -;

In column 3, line 60, " Bcl-$x_L$" should be - - Bcl-$X_L$ - -;

In column 5, line 26, "twenty-live" should be - - twenty-five - -;

In column 7, line 33, " Bcl-$x_L$" should be - - Bcl-$X_L$ - -;

In column 7, line 34, " Bcl-$x_L$" should be - - Bcl-$X_L$ - -;

In column 7, line 53, " Bcl-$x_L$" should be - - Bcl-$X_L$ - -;

In column 7, line 61, " Bcl-$x_L$" should be - - Bcl-$X_L$ - -;

In column 8, line 3, " Bcl-$x_L$" should be - - Bcl-$X_L$ - -;

In column 8, line 64, "reterence" should be - - reference - -;

In column 10, line 46, "caiboxy" should be - - carboxy - -;

In column 12, line 22, "arc" should be - - are - -;

UNITED STATES PATENT AND TRADEMARK OFFICE
CERTIFICATE OF CORRECTION

PATENT NO : 5,834,234

DATED : 10 November 1998

INVENTOR(S) : GALLO, Gregory J.

Page 2 of 4

It is certified that error appears in the above-identified patent and that said Letters Patent are hereby corrected as shown below:

In column 13, line 66, "eukaiyotic" should be - - eukaryotic - -;

In column 17, line 48, "dilters" should be - - differs - -;

In column 19, line 14, "tnd" should be - - and - -;

In column 20, line 47, "nmay" should be - - may - -;

In column 21, line 18, "CDNA" should be - - cDNA - -;

In column 23, line 32, "Mib" should be - - mAb - -;

In column 23, line 38, "*NucL*" should be - - *Nucl* - -;

In column 24, line 44, "forrnat" should be - - format - -;

In column 26, line 55, "o-phtaldehyde" should be - - o-phthalaldehyde - -;

In column 26, line 55, "imidaxole" should be - - imidazole - -;

In column 27, line 63, "ke V" should be - - Kev - -;

UNITED STATES PATENT AND TRADEMARK OFFICE
CERTIFICATE OF CORRECTION

PATENT NO. : 5,834,234

DATED : 10 November 1998

INVENTOR(S) : GALLO, Gregory J.

It is certified that error appears in the above-identified patent and that said Letters Patent is hereby corrected as shown below:

In column 28, line 5, "racetic" should be -- raacetic --;

In column 28, line 46, "erythrol)oietin" should be -- erythropoietin --;

In column 31, line 66, "Alzhcimer" should be -- Alzheimer --;

In column 32, line 33 "hormonereceptor" should be -- hormone receptor --;

In column 32, line 36, "hon-one" should be -- hormone --;

In column 34, line 38, "oligo(dT cellulose)" should be

-- oligo(dT) cellulose --;

In column 35, line 26, "polymerasc" should be -- polymerase --;

In column 35, line 49, "Samnbrook" should be -- Sambrook --;

In column 36, line 47, Bcl-x$_L$" should be -- Bcl-X$_L$ --;

In column 37, line 61, "flourotgraphy" should be -- fluorography --;

UNITED STATES PATENT AND TRADEMARK OFFICE
CERTIFICATE OF CORRECTION

PATENT NO. : 5,834,234
DATED : 10 November 1998
INVENTOR(S) : GALLO, Gregory J.

It is certified that error appears in the above-identified patent and that said Letters Patent is hereby corrected as shown below:

In column 39, line 2, "abbenant" should be -- aberrant --;

In column 40, line 54, $Bcl-x_L$" should be -- $Bcl-X_L$ --;

In column 41, line 11, $Bcl-x_L$" should be -- $Bcl-X_L$ --;

In column 41, line 24, $Bcl-x_L$" should be -- $Bcl-X_L$ --;

In column 42, line 45, $Bcl-x_L$" should be -- $Bcl-X_L$ --; and

In column 57, line 35, "RH3 domain" should be -- BH3 domain --.

Signed and Sealed this

Thirtieth Day of May, 2000

Attest:

Q. TODD DICKINSON

*Attesting Officer*

*Director of Patents and Trademarks*